US008382737B2

(12) United States Patent
Yeakley et al.

(10) Patent No.: US 8,382,737 B2
(45) Date of Patent: Feb. 26, 2013

(54) MULTI-CHAMBER MIXTURE DISPENSING SYSTEM

(76) Inventors: Rourke M. Yeakley, Eagle, ID (US); Charles Leslie Floyd, Emeryville, CA (US)

( * ) Notice: Subject to any disclaimer, the term of this patent is extended or adjusted under 35 U.S.C. 154(b) by 0 days.

(21) Appl. No.: 13/477,651

(22) Filed: May 22, 2012

(65) Prior Publication Data

US 2012/0238951 A1 Sep. 20, 2012

Related U.S. Application Data

(62) Division of application No. 13/007,063, filed on Jan. 14, 2011, now Pat. No. 8,206,368.

(51) Int. Cl.
*A61B 19/00* (2006.01)
*A61M 5/32* (2006.01)
*A61M 37/00* (2006.01)

(52) U.S. Cl. .......................................... 604/416; 604/87

(58) Field of Classification Search .................. 604/205, 604/236, 403–416; 220/500, 501; 206/363–366; 222/80, 129, 386
See application file for complete search history.

(56) References Cited

U.S. PATENT DOCUMENTS 6,244,433 B1 * 6/2001 Vieu ............................ 206/221

* cited by examiner

*Primary Examiner* — Philip R Wiest
(74) *Attorney, Agent, or Firm* — Scott D. Swanson; Dykas & Shaver

(57) ABSTRACT

Disclosed is a dispensing system a dispenser having a first chamber containing a first material and a second chamber containing a second material. The dispenser is configured to selectively retract one of the chambers at least partially within the other to transition the dispenser between an extended position and a compact position. The first chamber includes an open top end that is, before use, covered with a first breakable membrane. A breaker ring, at least initially covered with a second breakable membrane, is configured to break the breakable membranes when the dispenser is transitioned between an extended position and a compact position. In the compact position, with the membranes broken, the first material and second material are free to form a mixture that can be dispensed via an opening in the dispenser's openable tip.

9 Claims, 27 Drawing Sheets

MULTI-CHAMBER MIXTURE DISPENSING SYSTEM

PRIORITY/CROSS-REFERENCE TO RELATED APPLICATIONS

This application is a divisional of application Ser. No. 12/007,0063 filed Jan. 14, 2011, entitled Multi-Chamber Mixture Dispensing System, which is pending, the disclosure of which is incorporated herein by reference, which is a continuation-in-part application of application Ser. No. 12/689,165, filed Jan. 18, 2010, entitled "Twistable Medication Dispensing System," which is issued U.S. Pat. No. 8,109, 917, the disclosure of which is incorporated herein by reference.

FIELD OF THE INVENTION

The invention generally relates to mixture dispensing systems and more particularly to a portable, pre-measured mixture dispensing system.

BACKGROUND OF THE INVENTION

One of the greatest benefits of modern medicine has been the ability of antibiotics and other medications to cure and treat diseases that have plagued mankind from the beginning of time. While many individuals have access to medications whose usage can be lifesaving, the availability and dispersal of these medications to individuals that truly need them throughout the world has not yet been properly established. One of the reasons for which the dispersal of medication has not been effective in all locations is that, in many locations, individuals do not know how much medication to impart to reach the desired dosing requirements for efficacy while also preventing damage to the individual. Another problem that occurs is that, in some instances, the ability to take the medication cannot be effectively performed because of a lack of dispensatory materials at the designated location.

Additionally, medication to be dispensed in small amounts is often sold in large containers and sent in shipments that may require refrigeration. Thus, the cost of a relatively small amount of medication is increased by the cost of transporting the medication to the desired location and storing the medication. In other instances, the individual needing to use medication is required to purchase a greater amount of medication than is actually needed. In these circumstances the cost of the more-than-needed medication can be prohibitive for the individual.

Further, the administration of medication often requires more time, knowledge, or precision than an individual is able to apply to the administration of medication. When this occurs, an individual could measure and utilize the medication inappropriately. As a result, individuals may become ill from taking too much of the medication or find that the medication is ineffective against the disease to be treated when improperly-small dosages of the medications are administered. This in turn can lead to a variety of otherwise-avoidable health issues including sickness, discomfort, pain, irritability, and even death to individuals who fail to take the proper medication at the proper times or in the proper amounts.

As a particular example, in treating bacterial inventions and other bio-hazards, including the defenses against organisms used as bio-weaponry, the improper use or dosing of antibiotics can lead to mutations of the bacteria involved, leading to the creation of medication-resistant bacteria that will not respond to the traditionally-outlined antibacterial regimens.

SUMMARY OF THE INVENTION

The present dispenser is a dispensing system for dispensing pre-measured doses of selected materials, particularly medications, in a safe and effective manner and in any of a variety of circumstances. The dispenser can be utilized by individuals with little to no medical training and without the need to measure medications to be dispensed.

The dispenser includes a first chamber containing a first material, such as a reconstituting liquid, and a second chamber containing a second material, such as a medication powder. The first chamber further has an open top end that is covered by a first breakable membrane. The second chamber has an openable tip, which, when opened defines an opening. Contained between the openable tip of the second chamber and the first breakable membrane is a breaker ring, the lower edge of which is covered by a second breakable membrane. The lower edge of the breaker ring is further configured to break both the first and second breakable membranes when the lower edge of the breaker ring is brought into forced contact with the breakable membranes.

The first chamber and second chamber are configured to connect and to selectively retract relative to one another, either by part of the first chamber retracting within part of the second chamber or by part of the second chamber retracting within part of the first chamber. By this retraction, such as by twistable retraction, the first chamber and second chamber are selectively transitionable between an extended position in which the lower edge of the breaker ring is not in contact with either the first breakable membrane or the first material within the first chamber, and a compact position, in which the lower edge of the breaker ring is received within the open top end of the first chamber.

Before use, and when the dispenser is in the extended position, the first breakable membrane and the second breakable membrane are intact, keeping the first material within the first chamber and the second material within the second chamber such that the two materials are not in contact with one another. In retracting the first chamber relative to the second chamber, or, contrarily, the second chamber relative to the first chamber, the lower edge of the breaker ring is brought into forcible contact with the second breakable membrane, eventually breaking open that membrane, and then into forcible contact with the first breakable membrane, eventually breaking open that membrane. With additional retraction, the lower edge of the breaker ring passes through the open top end of the first chamber bringing the dispenser to its compact position. In the compact position, the first material within the first chamber and the second material within the second chamber are able to mix within the two chambers of the dispenser, forming a mixture. When the openable tip is opened, the mixture can be forced out of the dispenser to be administered to a user, such as a patient.

Alternatively, the two chambers of the dispenser can be unconnected from one another and the material within the second chamber, which could be medication in a powder form, dispensed by breaking the second breakable membrane and then emptying the second chamber via the open bottom end of the chamber, without having to open the openable tip. Similarly, the material within the first chamber can be separately dispensed, when the two chambers of the dispenser are unconnected, by breaking the first breakable membrane and emptying the contents of the first chamber via the open top end of the first chamber.

The dispenser is further configured to be stored and transported within a storage container. The storage container is formed, at least in part, by a container wall. In some embodiments, a puncturing device protrudes from the container wall and is configured to enable puncturing of a puncturable openable tip in the second chamber by applying the openable tip against the puncturing device with some pressure. Accordingly, the user of the dispensing system need not have available a separate puncturing device.

In any regard, this dispenser allows a pre-measured dosage of medication to be administered without having to use separate medication delivery devices and without the necessity of separately or carefully measuring the material to be dispensed. Having the material to be dispensed contained within one device lessens the risk of spillage and waste of the material. Further, the dispenser is used with only easy manipulation of a simple and safe device as no external sharp objects need be utilized. Thus, the dispenser can be utilized in a broad variety of circumstances by individuals with little or no training, either in medicine or in use of the dispenser.

The purpose of the foregoing summary is to enable the public, and especially the scientists, engineers, and practitioners in the art who are not familiar with patent or legal terms or phraseology to determine quickly, from a cursory inspection, the nature and essence of the technical disclosure of the application. The summary is neither intended to define the invention of the application, which is measured by the claims, nor is it intended to be limiting as to the scope of the invention in any way.

Still other features and advantages of the claimed dispensing system will become readily apparent to those skilled in the art from the following detailed description describing preferred embodiments of the dispensing system, simply by way of illustration of the best mode contemplated by carrying out the dispensing system. As will be realized, the dispensing system is capable of modification in various obvious respects all without departing from the invention. Accordingly, the drawings and description of the preferred embodiments are to be regarded as illustrative, and not restrictive.

DESCRIPTION OF THE PREFERRED EMBODIMENTS

Figure 1:
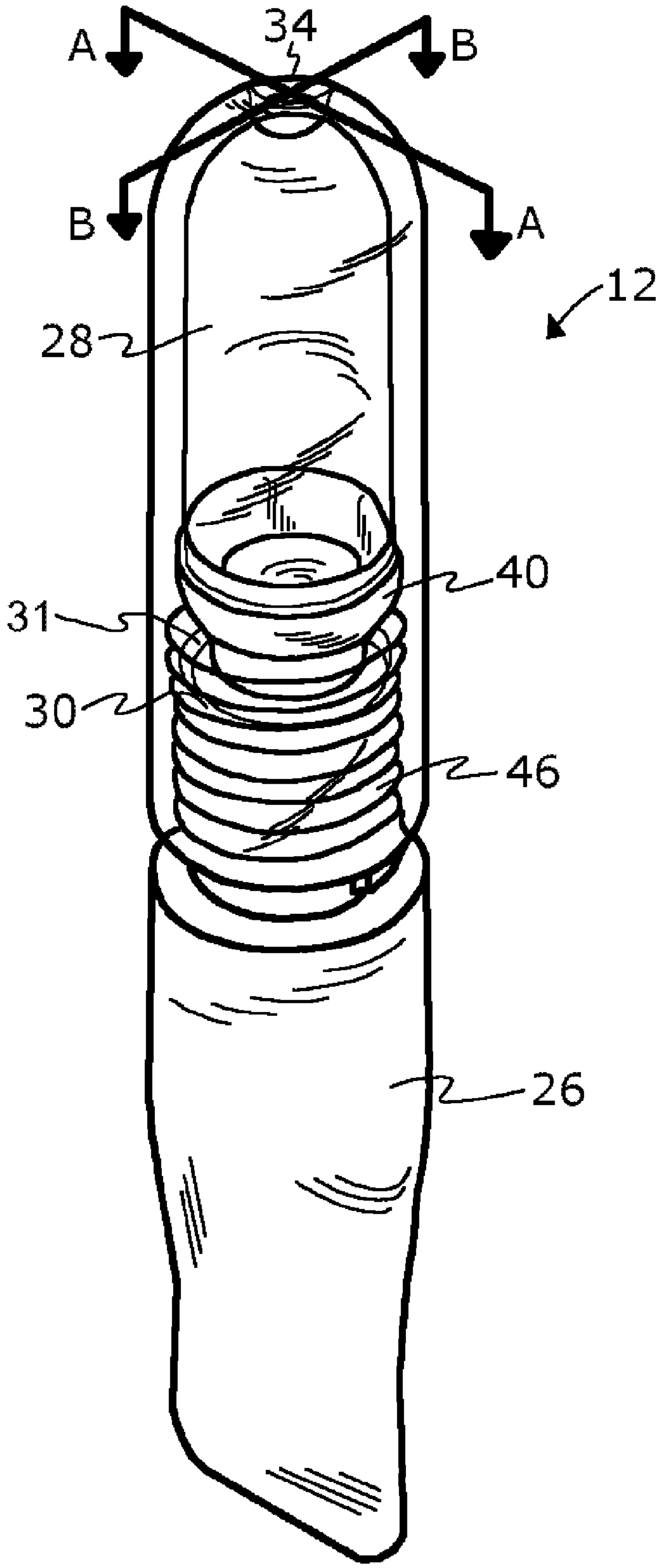
FIG. 1 is an isometric view of the front, top, and right sides of a medication dispenser according to a first embodiment of a dispensing system where the dispenser is in an extended position.
Figure 2:
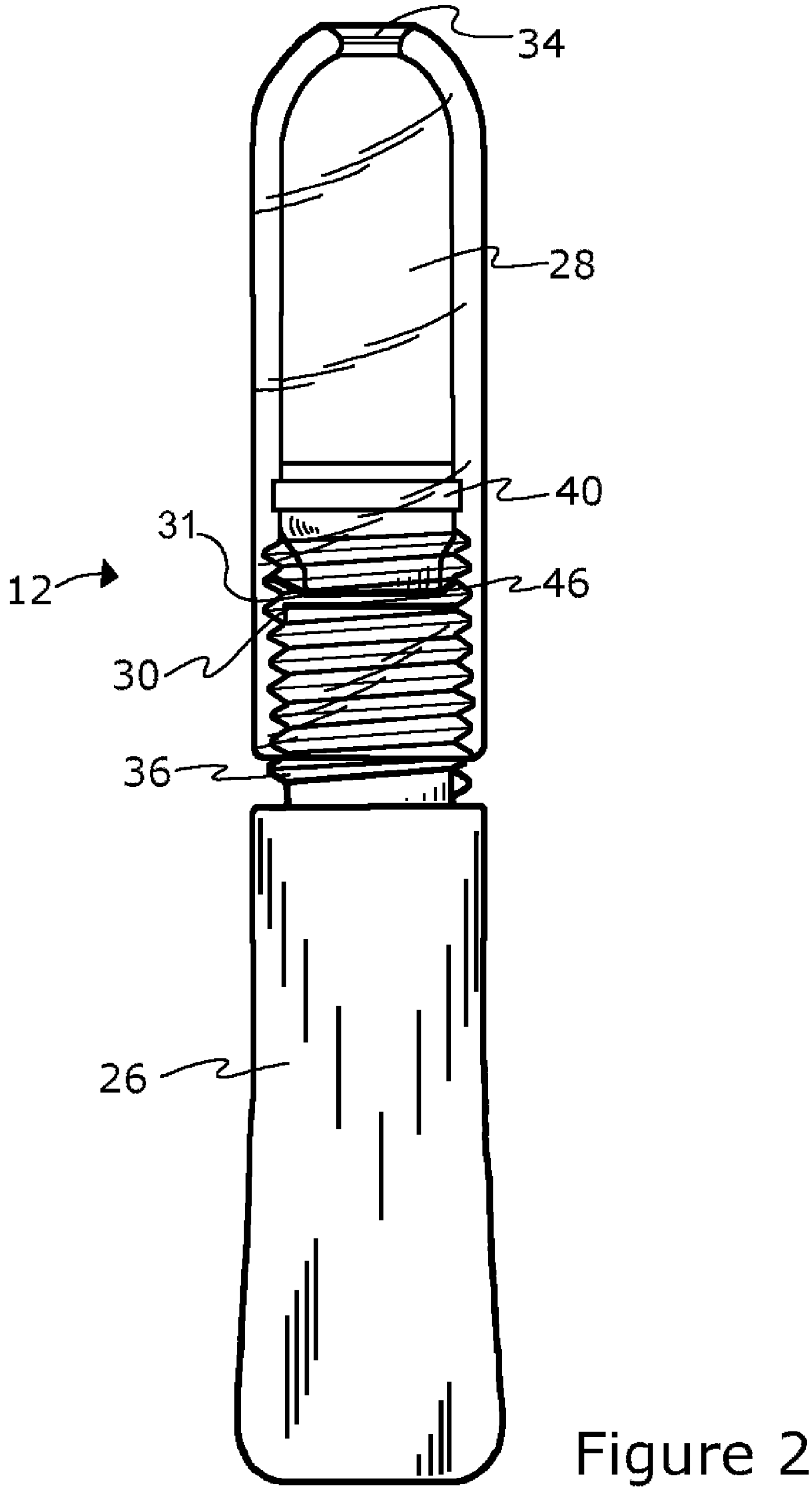
FIG. 2 is an elevation view of the front side of a medication dispenser according to the first embodiment of a dispensing system where the dispenser is in an extended position.
Figure 3:
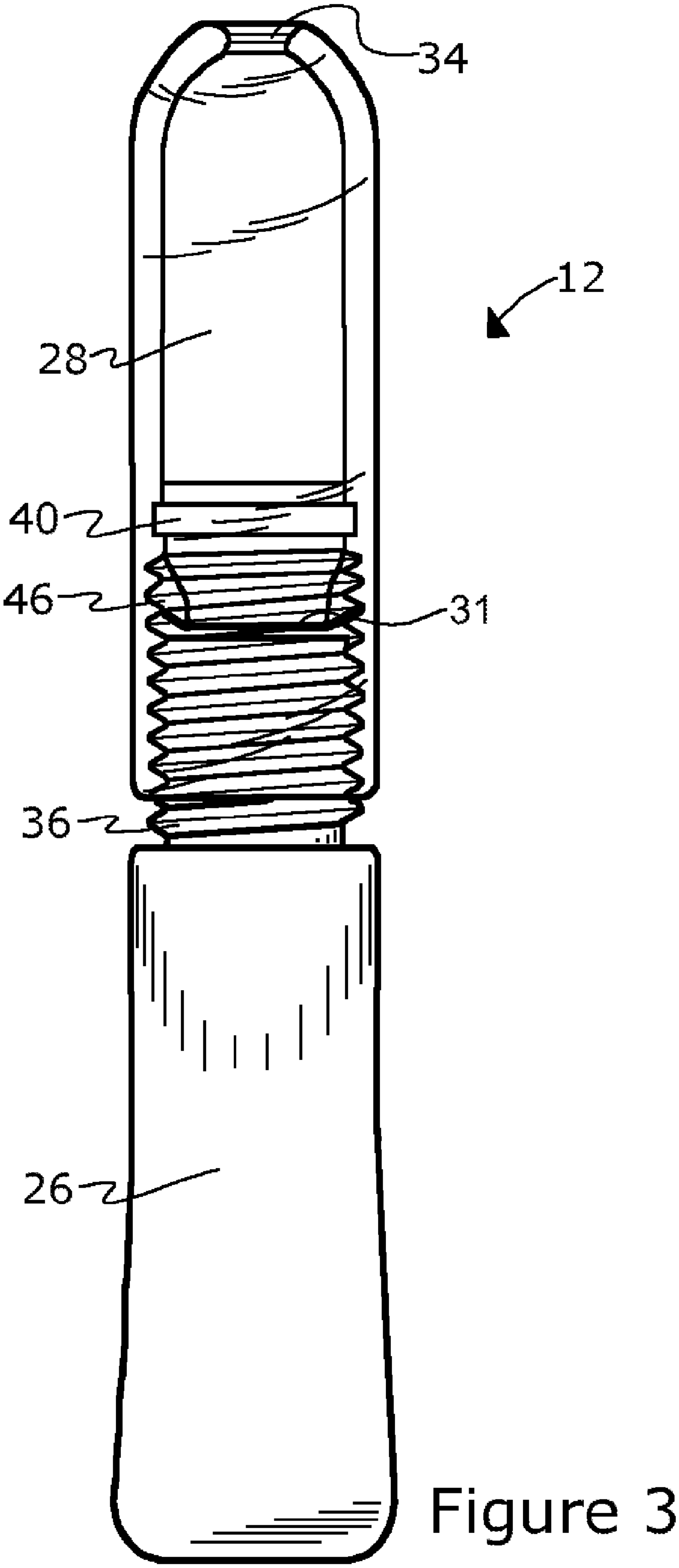
FIG. 3 is an elevation view of the back side of a medication dispenser according to the first embodiment of a dispensing system where the dispenser is in an extended position.
Figure 4:
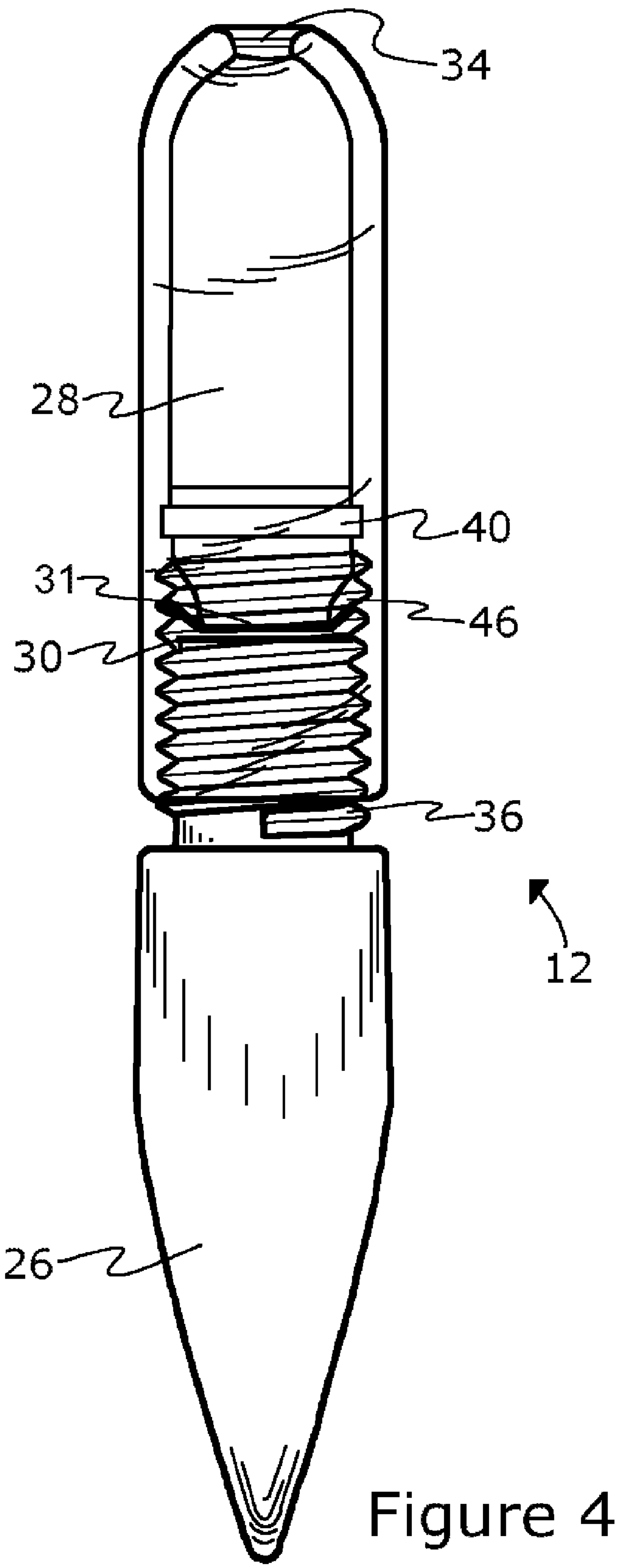
FIG. 4 is an elevation view of the right side of a medication dispenser according to the first embodiment of a dispensing system where the dispenser is in an extended position.
Figure 5:
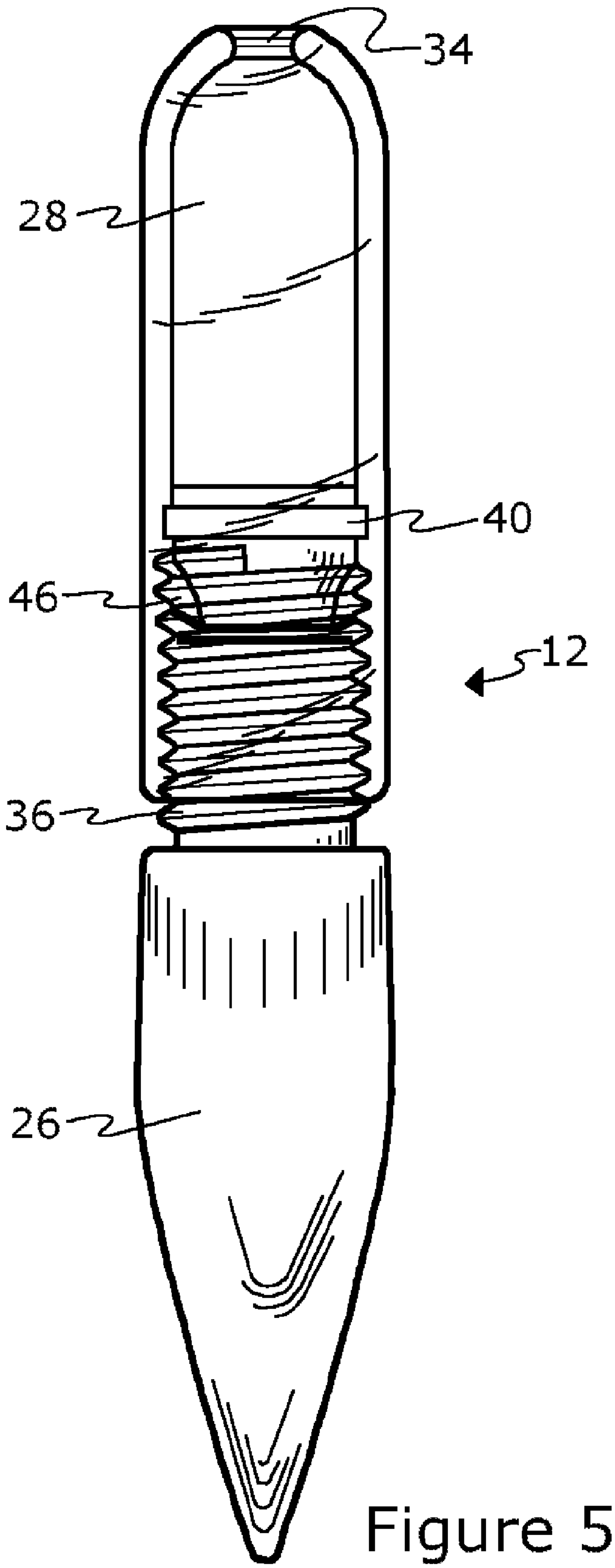
FIG. 5 is an elevation view of the left side of a medication dispenser according to the first embodiment of a dispensing system where the dispenser is in an extended position.
Figure 6:
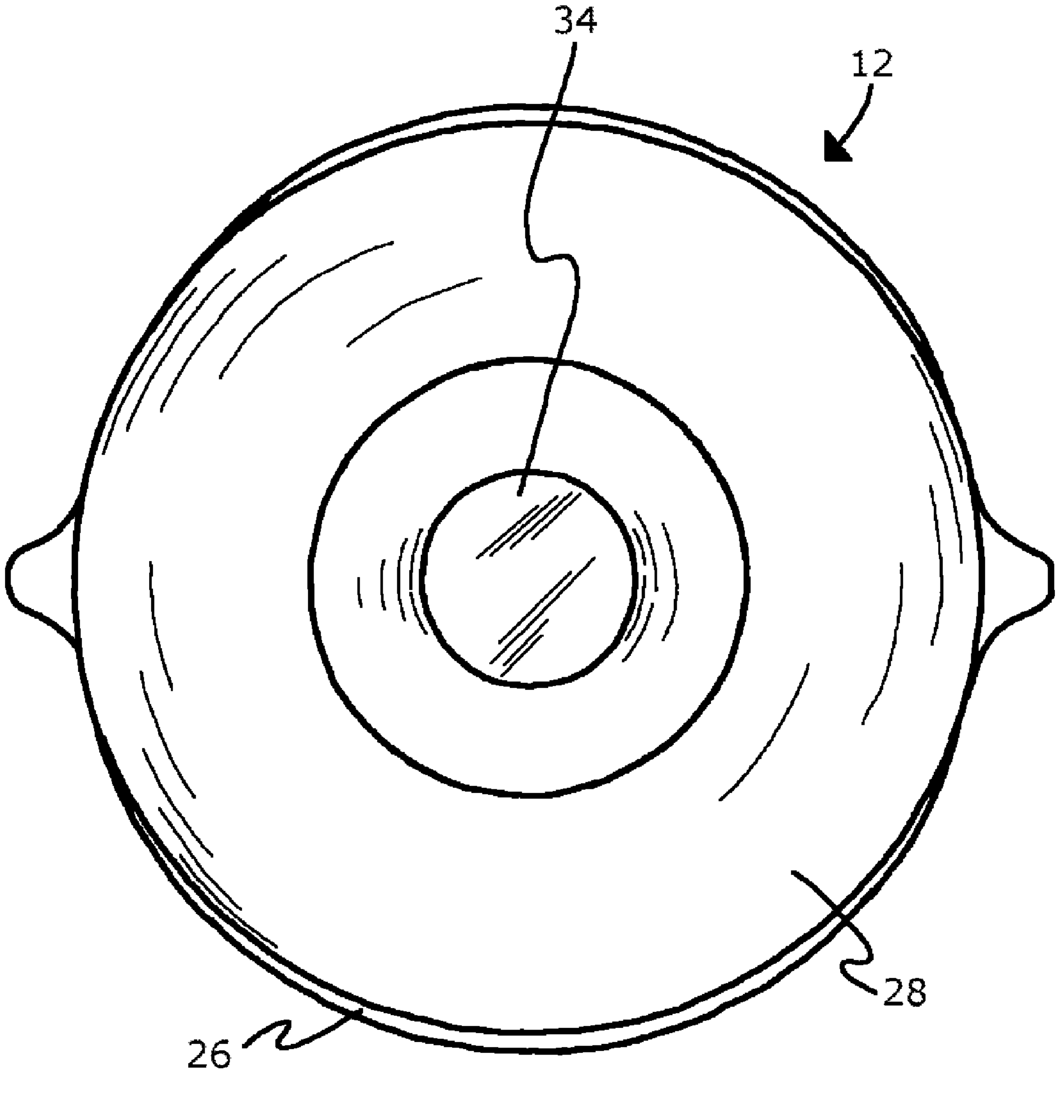
FIG. 6 is a plan view of the top side of a medication dispenser according to the first embodiment of a dispensing system.
Figure 7:
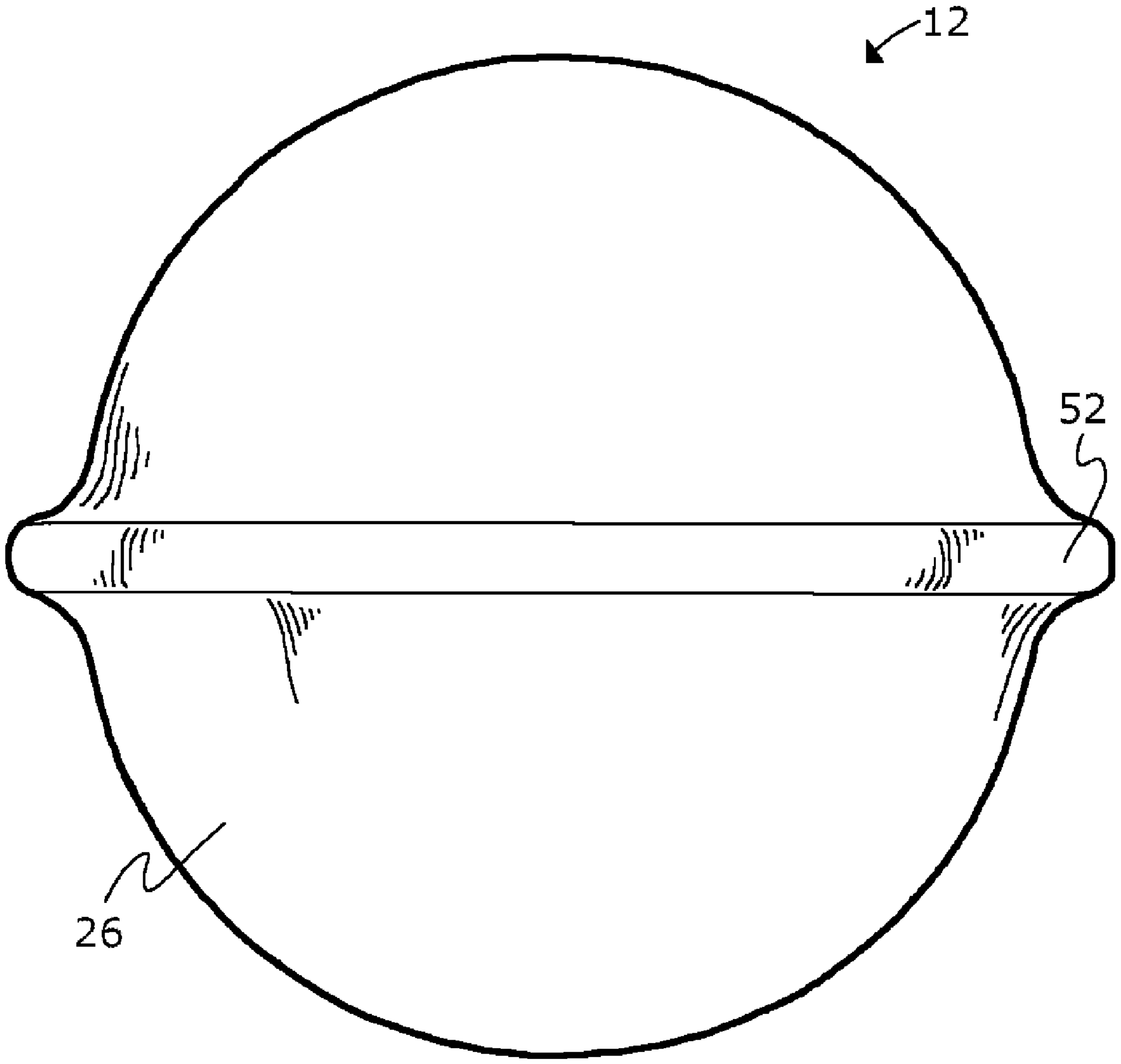
FIG. 7 is a plan view of the bottom side of a medication dispenser according to the first embodiment of a dispensing system.
Figure 8:
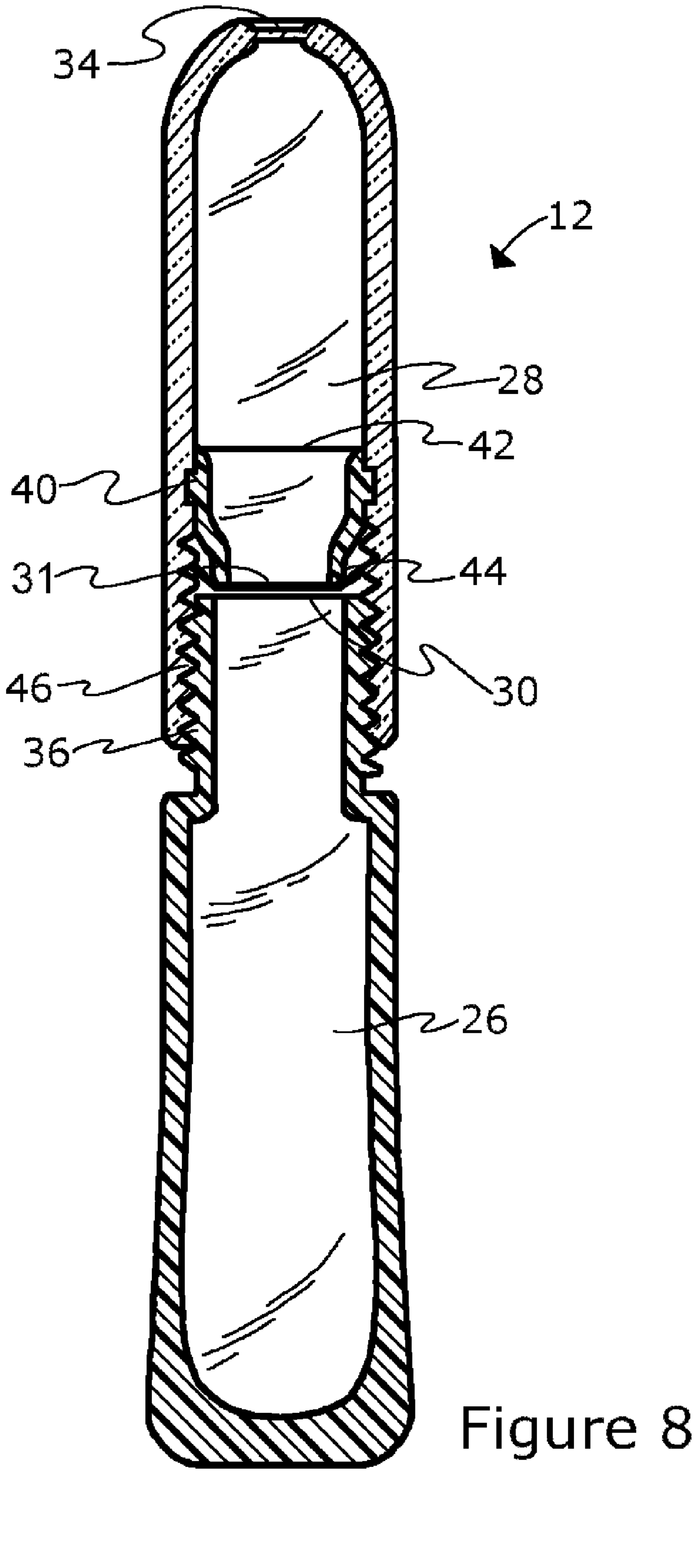
FIG. 8 is a cross-sectional, elevation view, taken along line A-A from the front side, of a medication dispenser according to the first embodiment of a dispensing system where the dispenser is in an extended position.

While the dispensing system is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the medication dispenser as defined in the claims.

As depicted in the drawings, embodiments of the dispensing system provide a system for storing, transporting, and eventually dispensing a pre-measured amount of a mixture of material, such as a medication mixture, where such mixture is originally stored in two separated containers. As such, medication in a solid, powder form can be kept separate from a reconstituting fluid, but in containers quickly and easily combined to provide for mixing of the substances before dispensing of the same without having to use separate dispensing devices and without having to have medical or technological training.

In the following description and in the figures, like elements are identified with like reference numerals. The use of "e.g.," "etc.," and "or" indicates non-exclusive alternatives without limitation unless otherwise noted. The use of "including" means "including, but not limited to," unless otherwise noted.

Figure 27:
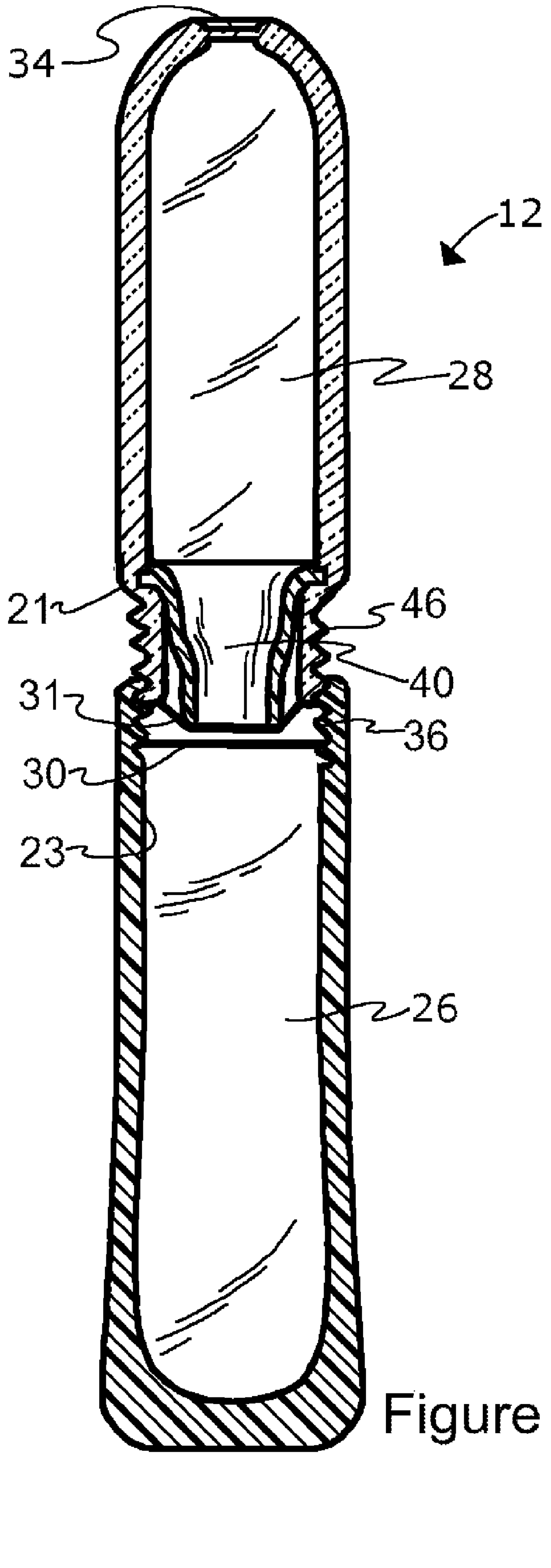
FIG. 27 is a cross-sectional, elevation view from the front side of a medication dispenser according to a fifth embodiment of a dispensing system where the dispenser is in an extended position.

As shown in the figures, the dispensing system includes a dispenser 12 and a storage container 80. According to a first embodiment, the dispenser 12 includes a first chamber 26 that has an open top end 24. According to the first through fourth embodiments, depicted in FIGS. 1 through 26, first screw threads 36 line an upper area of an external surface 22 of the first chamber 26. According to the fifth embodiment, depicted in FIG. 27, first screw threads 36 line an upper area of the internal surface 23 of the first chamber 26. Preferably, the first screw threads 36, according to the fifth embodiment, are recessed within the wall of the first chamber 26, as shown in FIG. 27. This minimizes the bulk of the first chamber 26 and thus the bulk of the dispenser 12 itself.

The first chamber 26 is at least partially compressible, preferably laterally compressible. At least before use, the first chamber 26 contains a first material, such as a fluid. According to the preferred embodiments, the first material is a fluid, specifically a reconstituting fluid 32. In some embodiments, such as the embodiment depicted in FIG. 18, the reconstituting fluid 32 is a liquid such as water. In other embodiments, the reconstituting fluid 32 is a gas such as air. Further, at least before use, the open top end 24 (shown in FIG. 11) is covered by a first breakable membrane 30 (shown in FIG. 10). The first breakable membrane 30 closes off the open top end 24 so that the reconstituting fluid 32 is contained within the first chamber 26.

Figure 13:
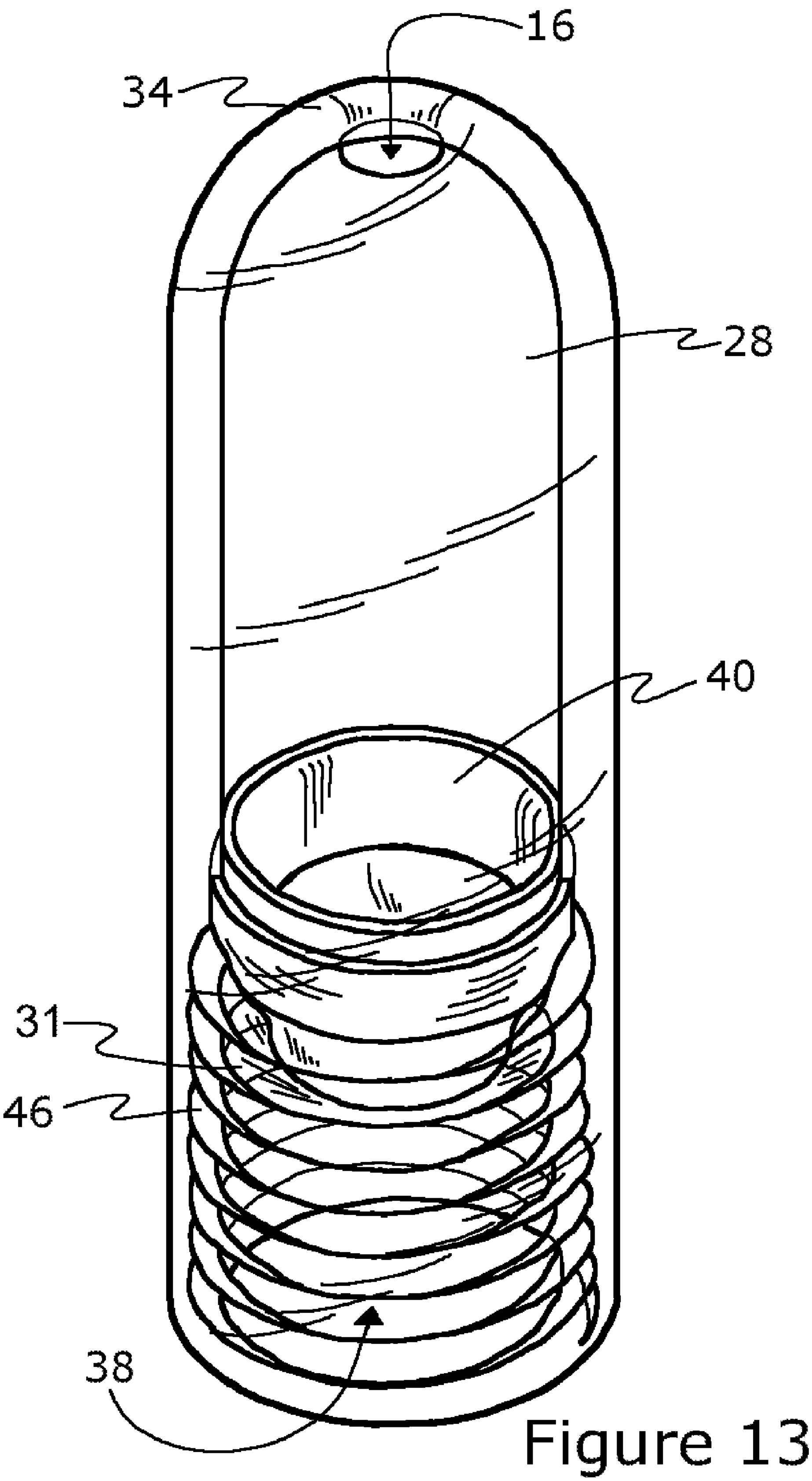
FIG. 13 is an isometric view of the front, top, and right sides of a second chamber and breaker ring of a medication dispenser according to the first embodiment of a dispensing system with the first breakable membrane removed.
Figure 14:
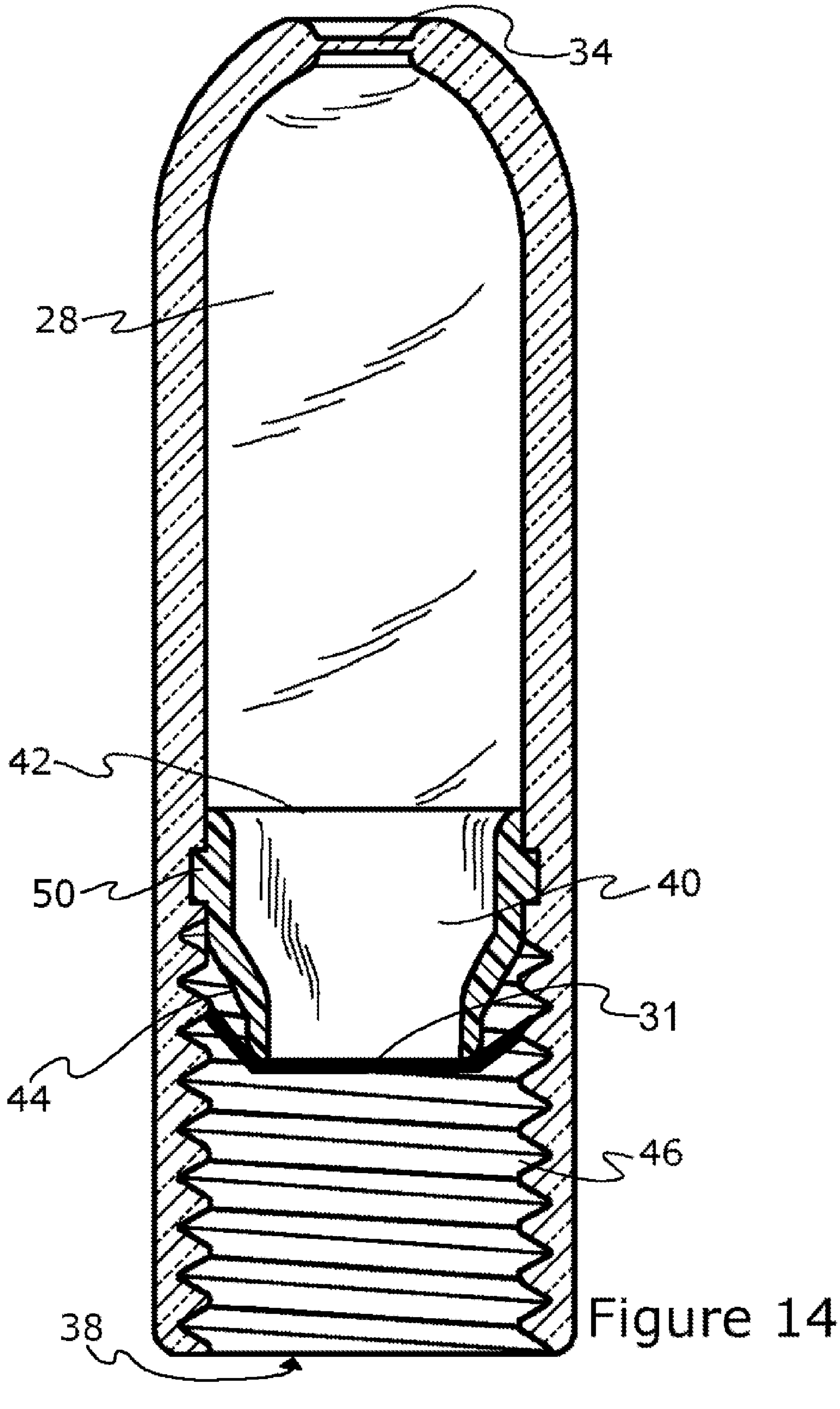
FIG. 14 is a cross-sectional, elevation view taken along line A-A from the left side, of a second chamber and breaker ring of a medication dispenser according to the first embodiment of a dispensing system.
Figure 15:
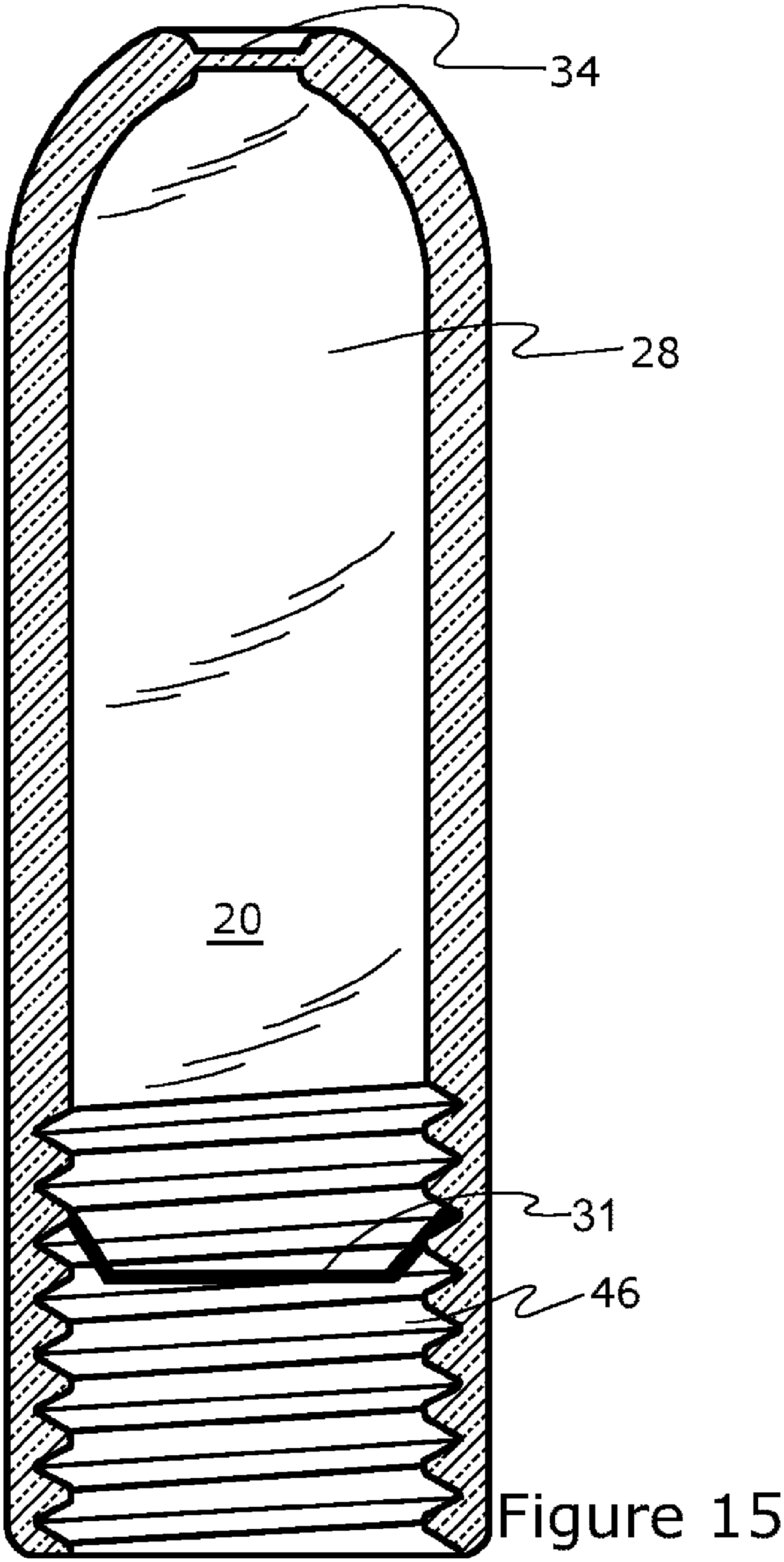
FIG. 15 is a cross-sectional, elevation view taken along line A-A from the left side, of a second chamber of a medication dispenser according to the first embodiment of a dispensing system.

The dispenser 12 of the depicted embodiments further includes a second chamber 28 that has an open bottom end 38 (shown in FIG. 13). According to the first through fourth embodiments, depicted in FIGS. 1 through 26, second screw threads 46 line a lower area of the internal surface 20 of the second chamber 28. Preferably, the second screw threads 46, according to the first through fourth embodiments, are recessed within the wall of the second chamber 28, as shown in FIG. 15. This minimizes the bulk of the second chamber 28 and thus the bulk of the dispenser 12 itself. According to the fifth embodiment, depicted in FIG. 27, second screw threads 46 line a lower area of the external surface 21 of the second chamber 28.

Figure 18:
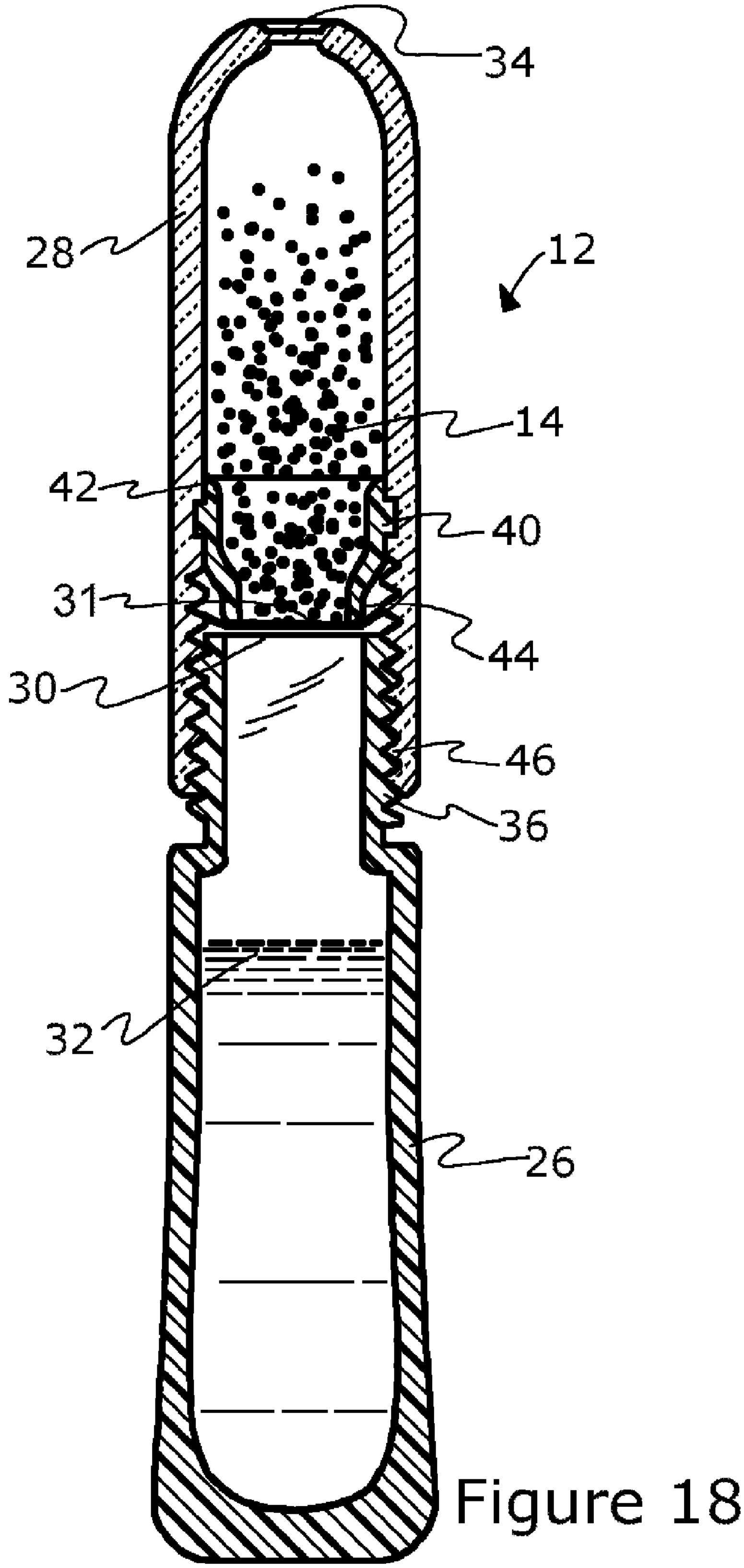
FIG. 18 is a cross-sectional, elevation view, taken along line A-A from the front side, of a medication dispenser containing medication and reconstituting fluid according to the first embodiment of a dispensing system where the dispenser is in an extended position.
Figure 19:
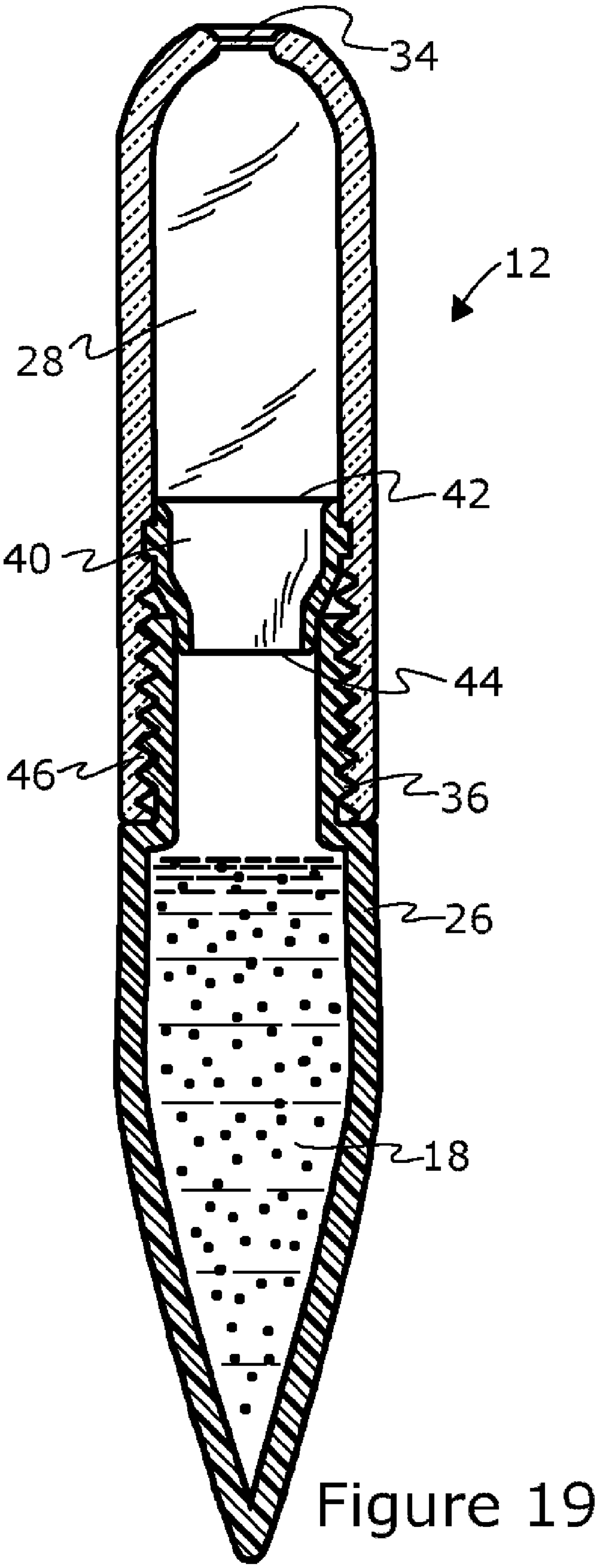
FIG. 19 is a cross-sectional, elevation view taken along line B-B from the right side, of a medication dispenser containing medication and reconstituting fluid according to the first embodiment of a dispensing system where the dispenser is in a compact position.

Contained within the second chamber 28 is a second material. According to some embodiments, the second material is a medication 14, preferably in a solid, powder form (as shown in FIG. 18). In other embodiments, the second material is a second fluid, such as a medication in liquid form.

The second chamber 28 further includes an openable tip 34, preferably at the upper-most portion of the second chamber 28. According to the first through third and fifth embodiments, the upper-most portion of the second chamber 28 is round, and the openable tip 34 is slightly recessed within the apex of the round upper-most portion. According to the fourth embodiment, depicted in FIG. 26, the second chamber 28 includes a tapering portion, preferably a tapering top portion 54, proximate to the openable tip 34, which is slightly recessed within the apex of the tapering portion 54. The tapering top 54 of the second chamber 28 of the fourth embodiment is configured to accommodate attachment of a catheter to the dispenser 12.

In the depicted embodiments, the openable tip 34 is a relatively thin layer plastic (shown in FIG. 14) that is puncturable to form an opening 16 (shown in FIGS. 13). In other embodiments, the openable tip 34 is an opening covered by a removable tab. In still other embodiments, the openable tip 34 is a relatively thin layer of plastic that can be removed by snipping off the openable tip 34 or by ripping off the openable tip 34. In further embodiments, the openable tip 34 is also fitted with an attachment configured to connect the dispenser 12 with an intravenous line.

Also, according to the depicted embodiments, the dispenser 12 further includes a breaker ring 40 situated between the openable tip 34 of the second chamber 28 and the first breakable membrane 30 of the first chamber 26. According to the embodiments shown in FIGS. 1 through 26, the breaker ring 40 is positioned within the second chamber 28, situated above the second screw threads 46. According to the embodiment shown in FIG. 27, the breaker ring 40 is positioned near the open bottom end 38 of the second chamber 28.

According to the depicted embodiments, the breaker ring 40 is fixedly connected to the internal surface 20 of the second chamber 28 via a peripheral protrusion 50. Preferably, the peripheral protrusion 50 comprises a ring protruding from the side of the breaker ring 40 where the circumference of the peripheral protrusion 50 is greater than the circumference of the wide upper edge 42. The peripheral protrusion 50 protrudes into and is received within the wall of the second chamber 28, as shown in FIG. 14. In some embodiments, the breaker ring 40 tapers from a wide upper edge 42 to a narrow lower edge 44, the peripheral protrusion 50 being located therebetween. According to the depicted embodiments, the circumference of the wide upper edge 42 is greater than the circumference of the narrow lower edge 44, and the breaker ring 40 is open at both the wide upper edge 42 and narrow lower edge 44. The narrow lower edge 44 is configured to be received within the open top end 24 of the first chamber 26. That is, preferably, the circumference of the exterior of the narrow lower edge 44 is less than the circumference of the interior of the open top end 24.

With particular attention to FIGS. 14 and 15, according to the depicted embodiments, the dispenser 12 further includes a second breakable membrane 31 that, at least initially, covers the lower edge 44 of the breaker ring 40. Preferably, the second breakable membrane 31 attaches, along its peripheral edge, to the internal surface 20 of the second chamber 28, as shown in FIG. 15. With the breaker ring 40 in place between the openable tip 34 and the first breakable membrane 30 covering the open top end 24 of the first chamber 26, the lower edge 44 of the breaker ring 40 is directed away from the openable tip 34 and toward the second breakable membrane 31 and the first breakable membrane 30.

The first chamber 26 and the second chamber 28 are configured to be selectively joinable. According to the depicted embodiment, the second screw threads 46 of the second chamber 28 are configured to correspond with the first screw threads 36 of the first chamber 26 such that the second chamber 28 and first chamber 26 are configured to be selectively joinable to one another via interaction of the first screw threads 36 and second screw threads 46. Correspondingly, the first chamber 26 and second chamber 28 are configured to be selectively disconnected from one another via interaction of the first screw threads 36 and the second screw threads 46. For example, in some embodiments, the screw threads 36, 46 are configured such that a clockwise rotation of the first chamber 26 relative to the second chamber 28 will draw the two chambers 26, 28 into closer proximity with one another while a counterclockwise rotation of the first chamber 26 relative to the second chamber 28 will move the two chambers 26, 28 further away from one another, eventually disconnecting the chambers 26, 28 from one another. As shown in the figures, twisting the second chamber 28 relative to the first chamber 26 to join the two together effectively unifies the second chamber 28 and the first chamber 26 such that the material therein is contained fully within the dispenser 12.

According to the embodiments depicted in FIGS. 1 through 26, the first chamber 26 is configured to selectively retract at least partially within the second chamber 28. As shown in FIG. 1 through 26, the upper-most portion of the first chamber 26, which area is lined with first screw threads 36 lining part of the external surface 22 of the first chamber 26, is configured to be retracted within the lower-most portion of the second chamber 28, which area is lined with second screw threads 46 lining part of the internal surface 20 of the second chamber 28. Selectively, partially retracting the first chamber 26 within the second chamber 28 transitions the dispenser 12 between an extended position, shown in FIGS. 1 through 5 and 18, and a compact position, shown in FIGS. 9 and 18.

According to the embodiment depicted in FIG. 27, the second chamber is configured to selectively retract at least partially within the first chamber 26. As shown in FIG. 27, the lower-most portion of the second chamber 28, which area is lined with second screw threads 46 lining part of the external surface 21 of the second chamber 26, is configured to be retracted within the upper-most portion of the first chamber 26, which area is lined with first screw threads 36 lining part of the internal surface 23 of the first chamber 26. Selectively, partially retracting the second chamber 28 within the first chamber 26 transitions the dispenser 12 between an extended position, like that shown in FIGS. 1 through 5 and 18, and a compact position, like that shown in FIGS. 9 and 18.

Ideally, during transport and storage, at least before use, the first chamber 26 and second chamber 28 are joined and arranged in an extended position, shown in FIGS. 1 through 5, 18, or 27, in which the narrow lower edge 44 of the breaker ring 40 is not in contact with the material within first chamber 26 and not in contact with the first breakable membrane 30. According to the embodiments depicted in FIGS. 1 through 5 and 18, the lower edge 44 of the breaker ring 40, of the dispenser 12 in the extended position, is external to the second chamber 28. The first chamber 26 and second chamber 28 are further retractable relative to one another to bring the lower edge 44 of the breaker ring 40 into closer proximity to the first breakable membrane 30. According to the depicted embodiments, more specifically, the first chamber 26 and second chamber 28 are further twistable relative, via interaction of the second screw threads 46 and first screw threads 36.

Figure 9:
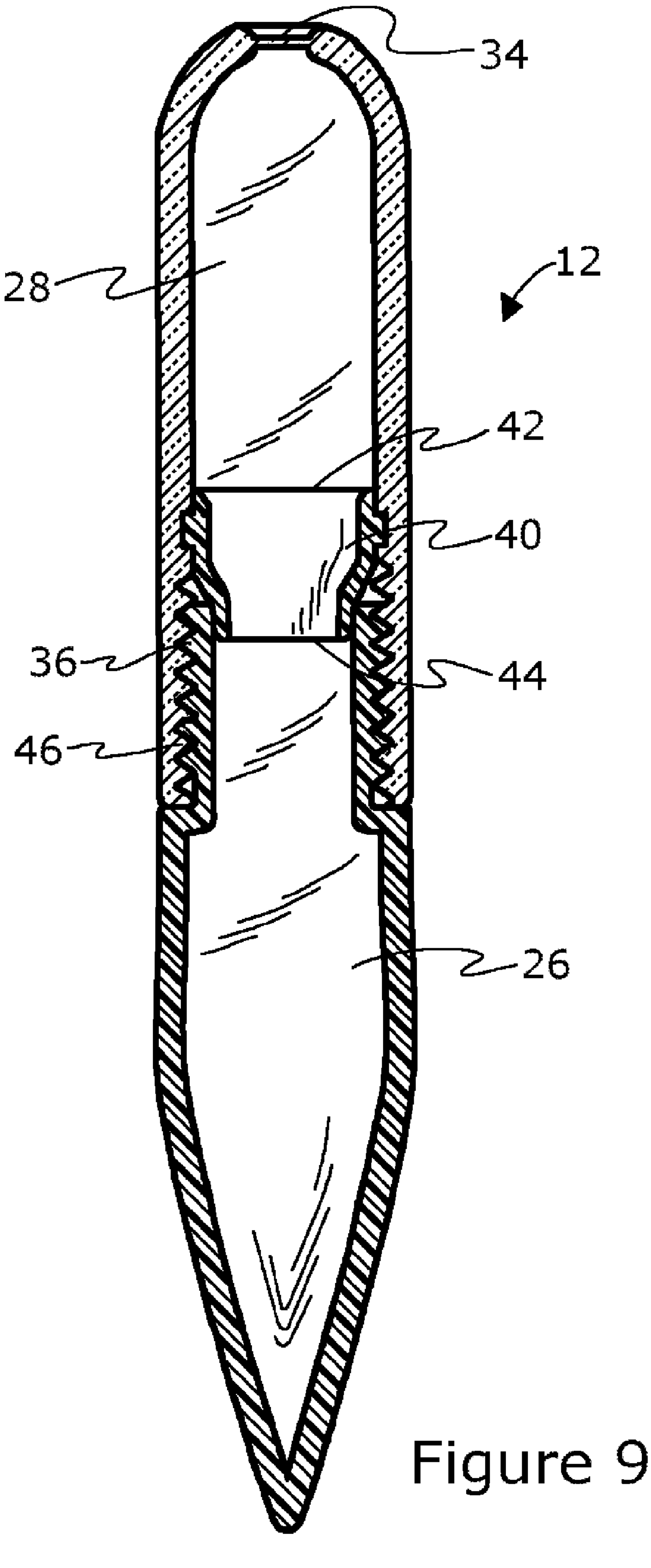
FIG. 9 is a cross-sectional, elevation view taken along line B-B from the right side, of a medication dispenser according to the first embodiment of a dispensing system where the dispenser is in a compact position.
Figure 10:
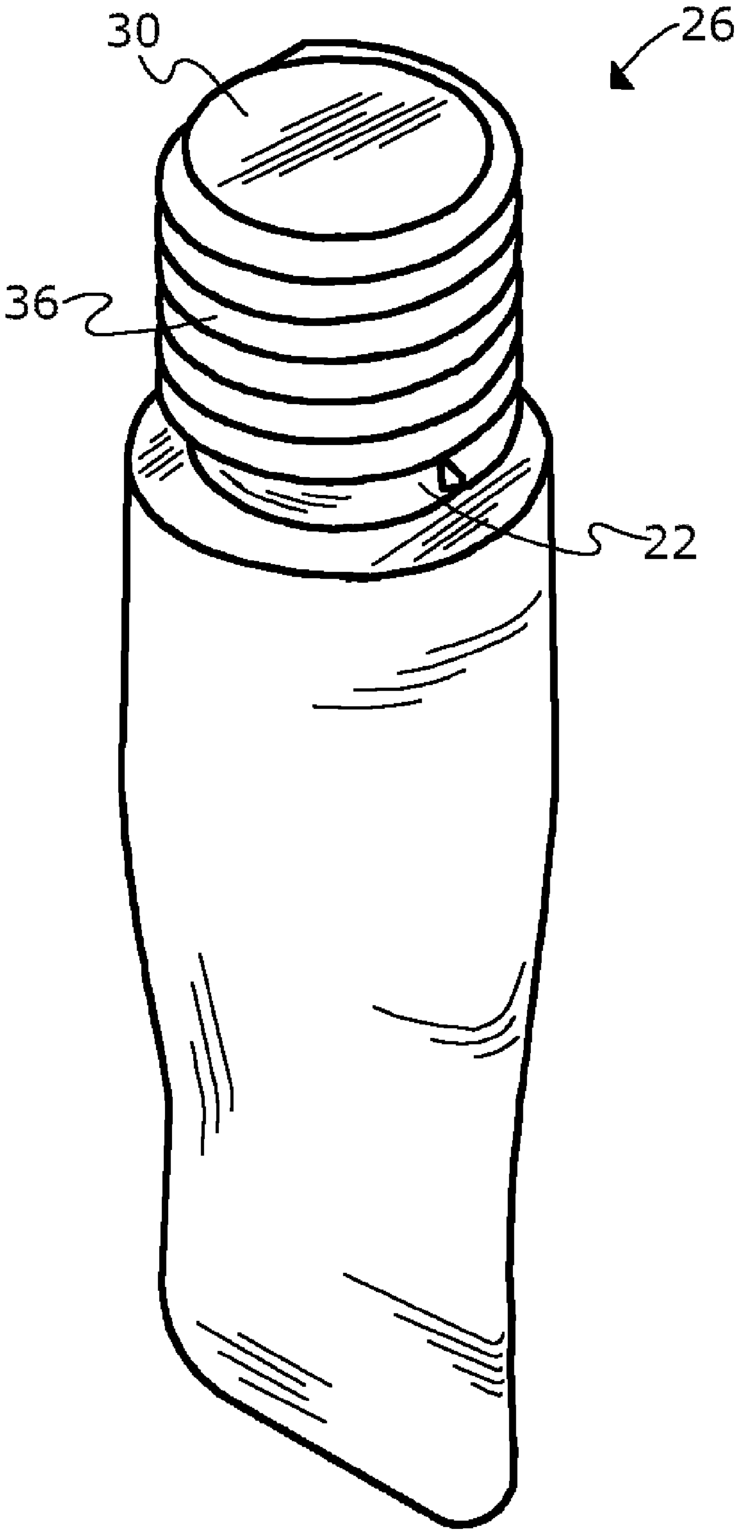
FIG. 10 is an isometric view of the front, top, and right sides of a first chamber of a medication dispenser according to the first embodiment of a dispensing system.
Figure 11:
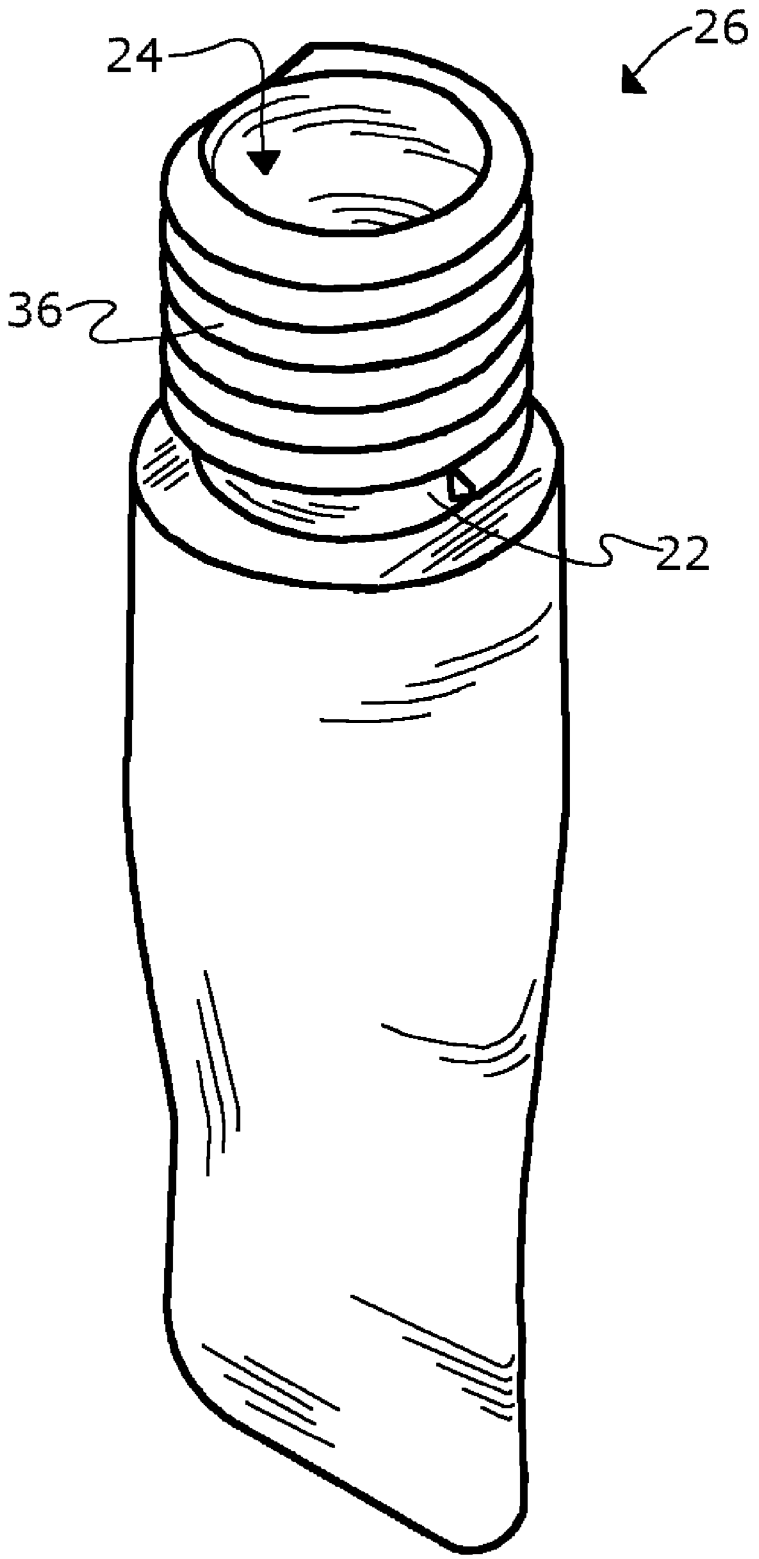
FIG. 11 is an isometric view of the front, top, and right sides of a first chamber of a medication dispenser according to the first embodiment of a dispensing system with the first breakable membrane removed.
Figure 12:
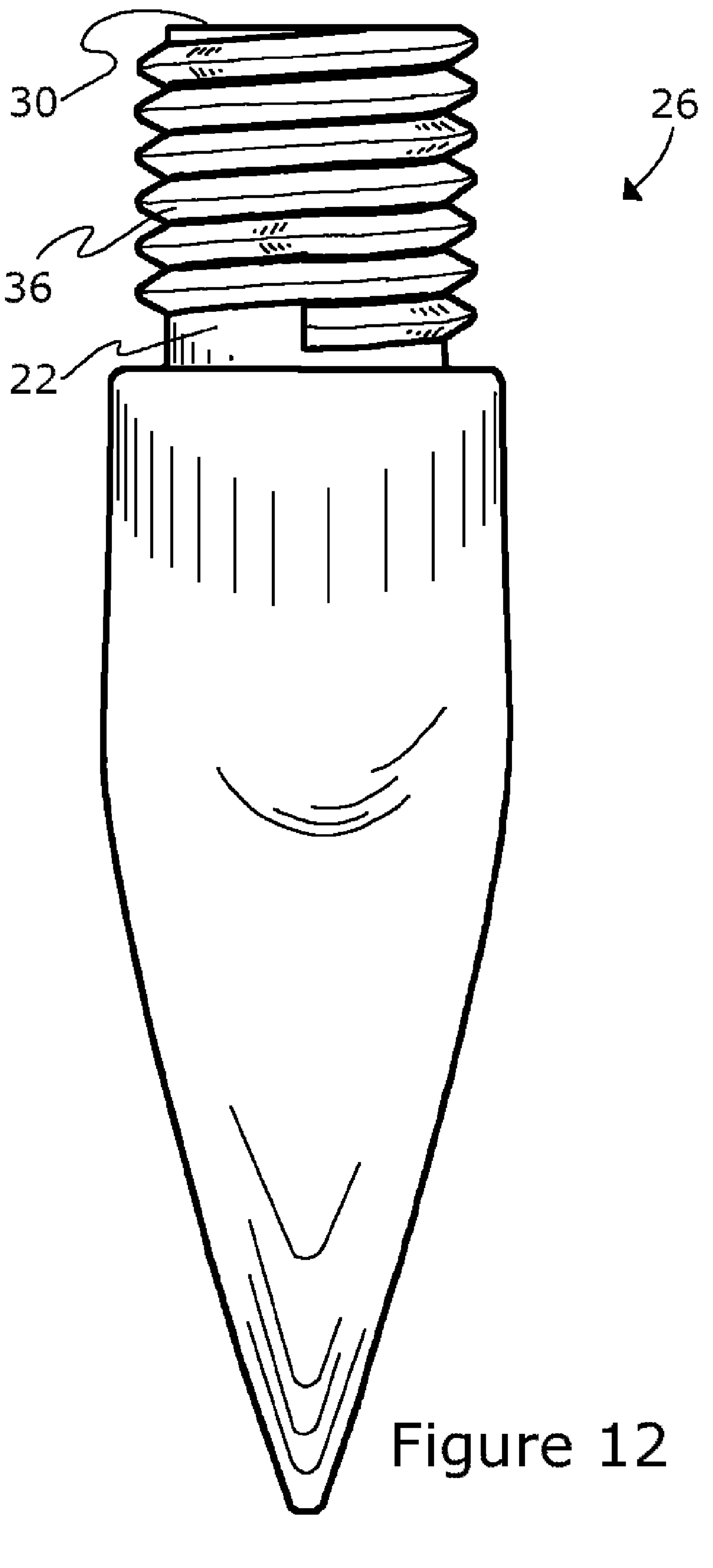
FIG. 12 is an elevation view of the right side of a first chamber of a medication dispenser according to the first embodiment of a dispensing system.

Enough selective retracting, whether by twisting, sliding, or other means, according to the embodiment, eventually transitions the dispenser 12 to a compact position, shown in FIGS. 9 and 18. In the compact position, the narrow lower edge 44 of the breaker ring 40 is received within the open top end 24 of the first chamber 26.

During retracting of the first chamber 26 and second chamber 28 relative to one another to transition the dispenser 12 from the extended position to the compact position, the narrow lower edge 44 of the breaker ring 40 is brought into forced contact with the second breakable membrane 31 covering the lower edge 44 of the breaker 40. Retracting past that point causes the narrow lower edge 44 of the breaker ring 40 to eventually break the second breakable membrane 31. Additional retracting brings the lower edge 44 of the breaker ring 40 into contact with the first breakable membrane 30 covering the open top end 24 of the first chamber 26. Still additional retracting results in the narrow lower edge 44 breaking the first breakable membrane 30.

Once the second breakable membrane 31 and the first breakable membrane 30 are broken, the first chamber 26 and second chamber 28 form a joined chamber within the dispenser 12. Accordingly, the second material, such as medication 14, that was originally contained within the second chamber 28 and the first material, such as reconstituting fluid 32, that was originally contained with the first chamber 26 can mix and form a mixture, such as a medication mixture 18. Ideally, the medication 14 may be shaken or otherwise agitated to encourage mixing of the medication 14 and reconstituting fluid 32 between the two chambers 26, 28.

It is further preferable that the first chamber 26 and second chamber 28 form a fluid-tight seal once joined. According to the depicted embodiments, then, the first screw threads 36 of the first chamber 26 and the second screw threads 46 of the second chamber 28 are configured to form a fluid-tight seal so that, once the first breakable membrane 30 and second breakable membrane 31 are broken, none of the reconstituting fluid 32 or medication mixture 18 will unintentionally leave the dispenser 12.

Figure 16:
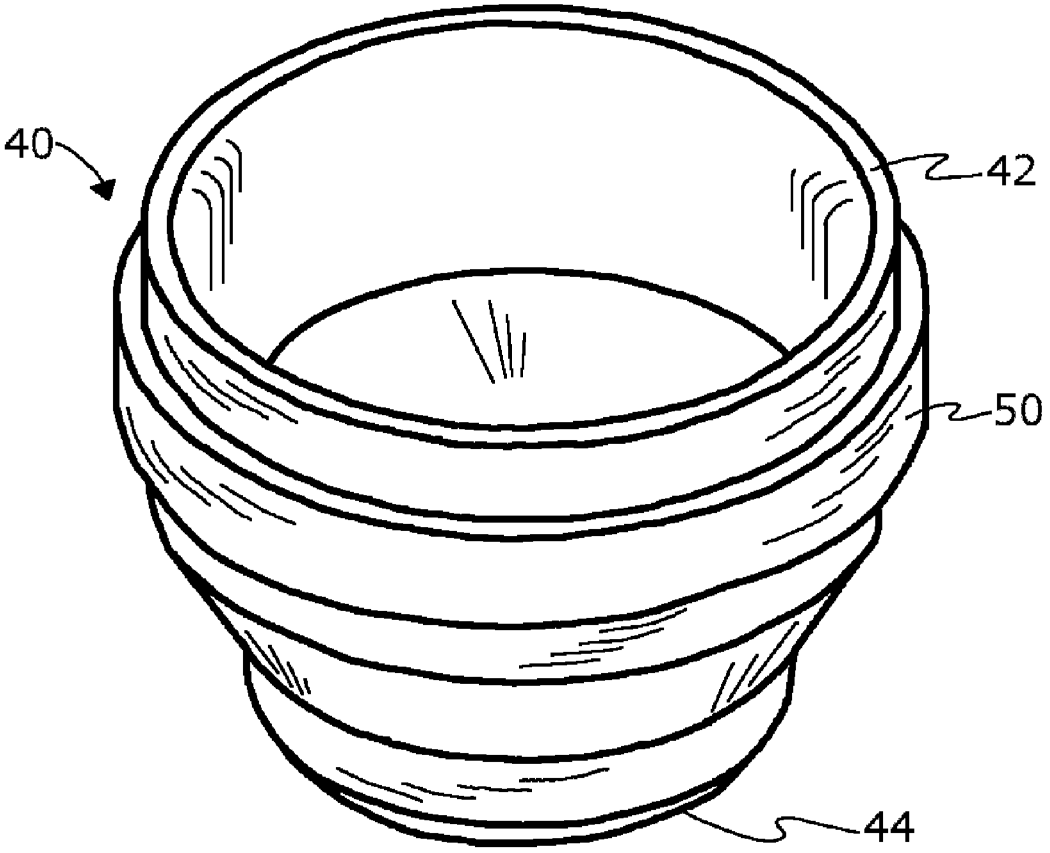
FIG. 16 is an isometric view of the front and top sides of a breaker ring of a medication dispenser according to the first embodiment of a dispensing system.
Figure 17:
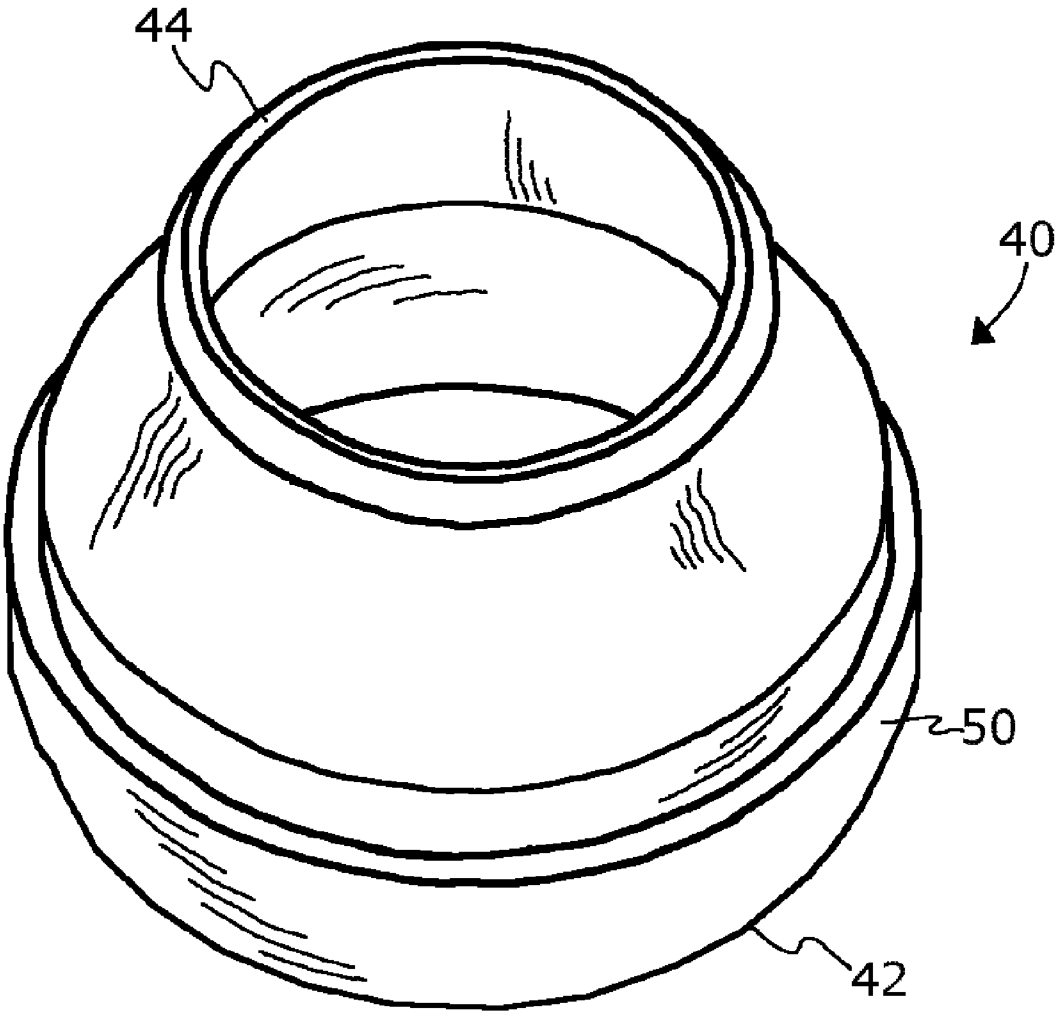
FIG. 17 is an isometric view of the back and bottom sides of a breaker ring of a medication dispenser according to the first embodiment of a dispensing system.

The breaker ring 40 of the first depicted embodiment, shown in FIGS. 16 and 17, includes a narrow lower edge 44 that is smooth and even along its edge. According to the first depicted embodiment, the narrow lower edge 44 defines a lower plane that is essentially parallel to an upper plane defined by the wide upper edge 42. Such lower plane and upper plane are also essentially parallel to the middle plane defined by the peripheral protrusion 50.

Figure 20:
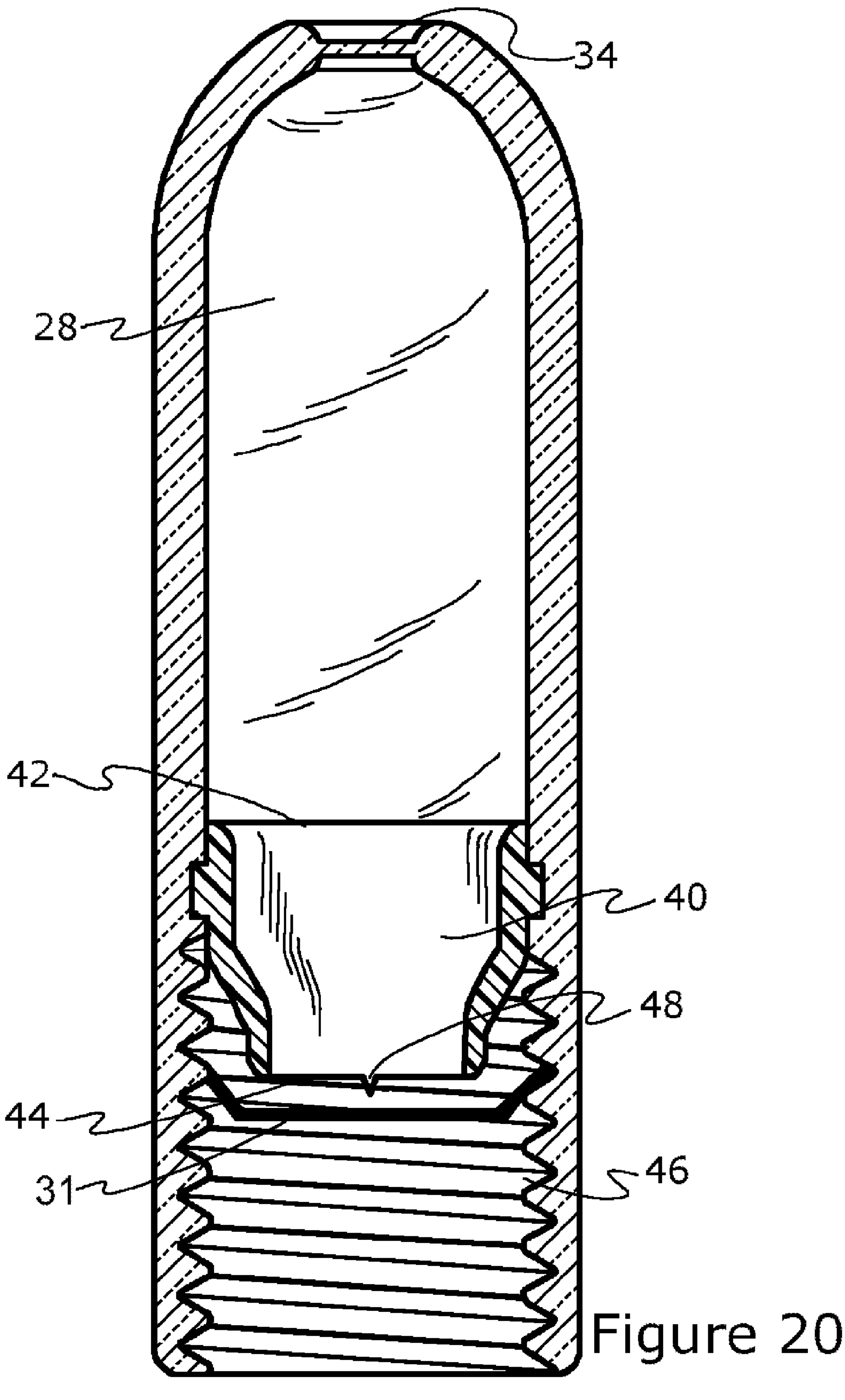
FIG. 20 is cross-sectional, elevation view taken along line A-A from the left side, of a second chamber and breaker ring of a medication dispenser according to the second embodiment of a dispensing system.
Figure 21:
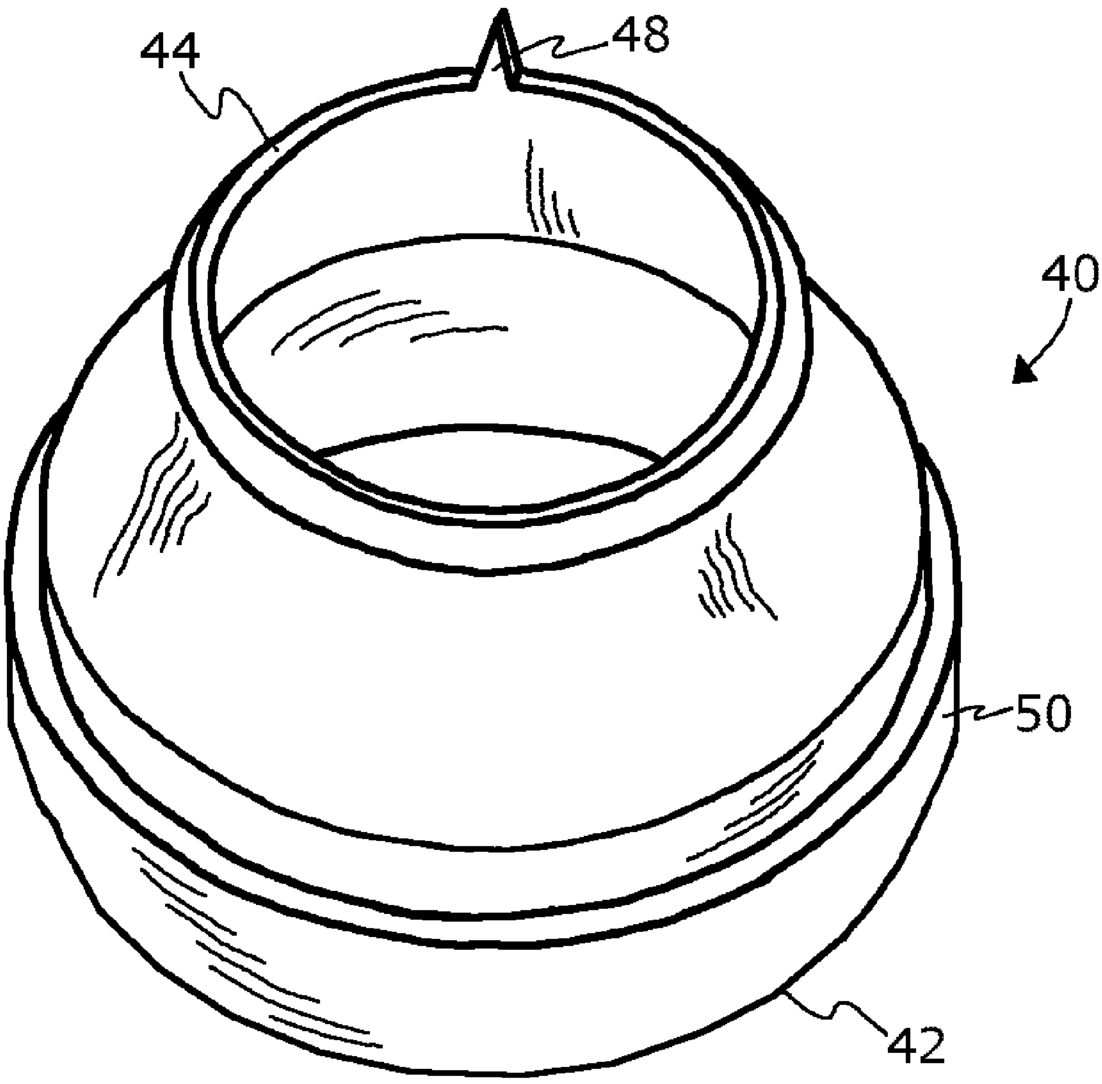
FIG. 21 is an isometric view of the back and bottom sides of a breaker ring of a medication dispenser according to the second embodiment of a dispensing system.

The breaker ring 40 of the second depicted embodiment, shown in FIGS. 20 and 21, includes a narrow lower edge 44 that has a protruding member 48. The protruding member 48 is configured to break the first breakable membrane 30 upon forced contact with the first breakable membrane 30. Preferably, the protruding member 48 is a sharp point. As such, forced contact of the tip of the sharp point with the first breakable membrane 30 or with the second breakable membrane 31 will result in first a puncturing of the second breakable membrane 31, followed by general breakage of the second breakable membrane 31, followed by a puncturing of the first breakable membrane 30, and then followed by a general breakage of the first breakable membrane 30 as the breaker ring 40 is brought into further forced contact with the first breakable membrane 30 as the first chamber 26 and second chamber 28 are retracted relative to one another. In other embodiments, the breaker ring 40 includes a number of protruding members 48 along the narrow lower edge 44.

Figure 22:
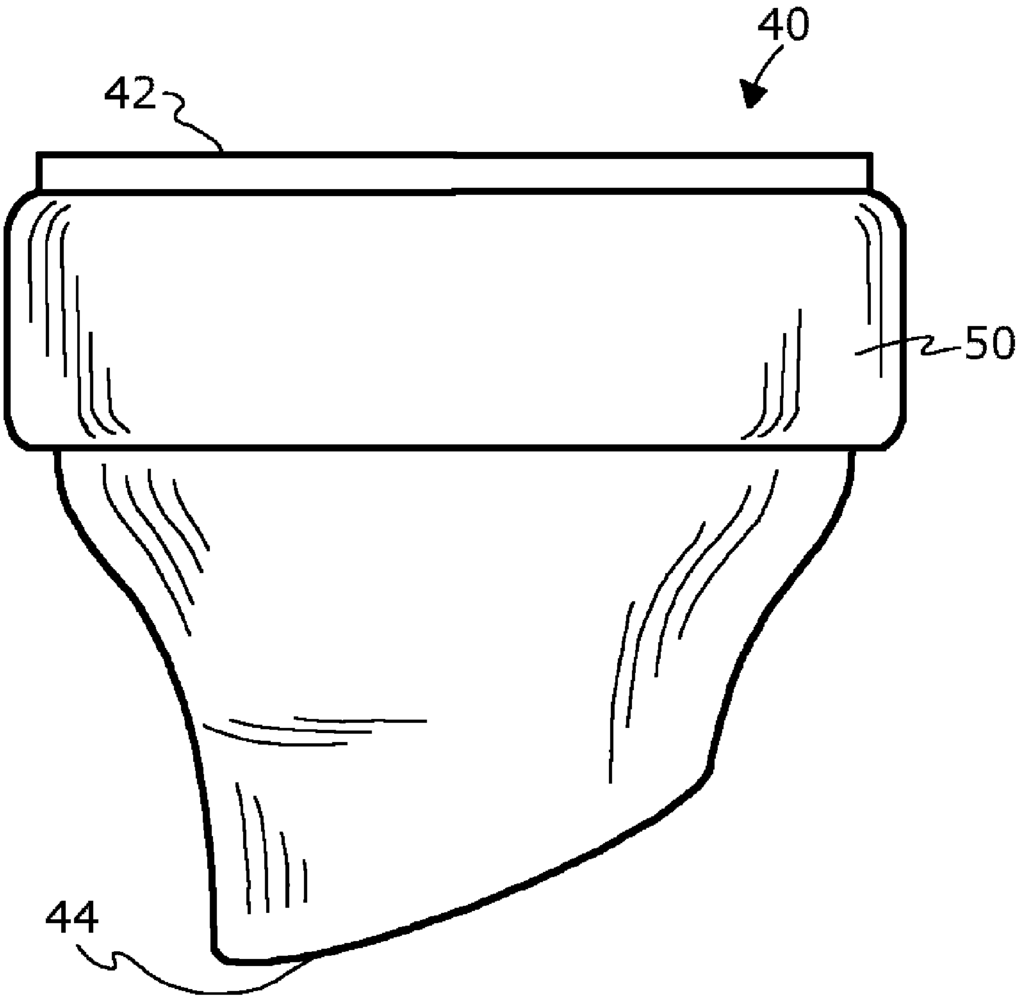
FIG. 22 is an elevation view of the front side of a breaker ring of a medication dispenser according to a third embodiment of a dispensing system.

The breaker ring 40 of the third depicted embodiment, shown in FIG. 22, includes a narrow lower edge 44 that is smooth and even along its edge. Further the narrow lower edge 44 defines a lower plane that is not parallel to an upper plane defined by the wide upper edge 42. Rather, the narrow lower edge 44 of the breaker ring 40, according to the third depicted embodiment, slants such that one area of the narrow lower edge 44 will come into contact with the second breakable membrane 31 and then the first breakable membrane 30, before the other areas of the narrow lower edge 44 as the dispenser 12 is transitioned between the extended position and the compact position. As such, the forced interaction of the narrow lower edge 44 and the second breakable membrane 31 and then the first breakable membrane 30 will, at least at first, be concentrated on the lowest area of the narrow lower edge 44, encouraging breakage of the second breakable membrane 31 and then the first breakable membrane 30 in that area of contact.

To dispense the medication mixture 18 to a patient, once the second breakable membrane 31 and the first breakable membrane 30 are broken and the dispenser 12 retracted so that it is in the compact position, the openable tip 34 can be opened so as to form an opening 16. Thereafter, the first chamber 26 may be compressed so as to force the medication mixture 18 out of the first chamber 26, through the breaker ring 40, and out of the second chamber 28 via the opening 16. In some situations, the first chamber 26 is compressed due to physical squeezing of the first chamber 26. In other situations, the first chamber 26 is compressed due to the application of suction within the dispenser 12.

The dispenser 12 is further configured such that the material within the first chamber 26 can be dispensed without opening the openable 34. That is, the first chamber 26 and second chamber 28 can be selectively disconnected from one another via moving the first chamber 26 and the second chamber 28 in the opposite direction from that used to retracted the chambers 26, 28 relative to one another, such as, depending on the embodiment, via twisting in the opposite direction than one would twist to transition the dispenser 12 from the extended position to the compact position. This extending movement will eventually separate the two chambers 26, 28 from each other. Thereafter, the material within the second chamber 28, such as the medication 14, can be emptied via the open bottom end 38 after breaking the second breakable membrane 31 with means other than the breaker ring 40, such as by application of pressure with a finger or fingernail against the second breakable membrane 31 or with the use of a separate puncturing device, so as to make accessible the open bottom end 38 of the second chamber 28. Thereafter, the material within the second chamber 28 can be emptied via the open bottom end 38. Alternatively, the openable tip 34 may be opened to create an opening 16 so that the material within the second chamber 28 can be emptied via the opening 16.

Alternatively or additionally, with the first chamber 26 and the second chamber 28 separated, the first breakable membrane 30 can be broken with means other than the breaker ring 40, such as by application of pressure with a finger or fingernail against the first breakable membrane 30 or with the use of a separate puncturing device, so as to make accessible the open top end 24. Thereafter, the material within the first chamber 26 can be emptied via the open top end 24.

Accordingly, separation of the two chambers 26, 28 from one another provides an option for dispensing of the medication to a patient without mixing the materials 14, 32. Further, the separation of the two chambers 26, 28 allows a user to refill or replace material within one or the other chamber 26, 28 before or without mixing the materials. Likewise, either chamber 26, 28 may be replaced with a new chamber 26, 28 containing as-yet unmixed material.

In some embodiments, the dispenser 12 is configured to be disposable, such that after dispensing the medication mixture 18, the entire dispenser 12 can be discarded or recycled. In other embodiments, the dispenser 12 is configured to be reusable, such that the first chamber 26 and second chamber 28 are retracted relative to one another in such a manner as to transition the dispenser 12 from the compact position to the extended position and then to disconnect the second chamber 28 from the first chamber 26. The first chamber 26 is then refilled with reconstituting fluid 32 and a new first breakable membrane 30 put in place to cover the open top end 24. The opening 16 in the openable tip 34 is covered with a selectively removable tab and additional medication 14 filled into the second chamber 28. A new second breakable membrane 31 is then put in place to cover the lower edge 44 of the breaker ring 40. Thereafter, the refilled first chamber 26 and second chamber 28 are again rejoined into the extended position. This reuse may be repeated as desired.

According to the depicted embodiments, the medication 14 within the second chamber 28 is a solid powder. In other embodiments, the medication 14 is a medication in fluid form. In still other embodiments, the material within the second chamber 28 is a non-medicinal material. Further, according to the depicted embodiments, the second chamber 28 is made up of a translucent plastic that is noncompressible. Also according to the depicted embodiments, the first chamber 26 tapers in width along the lower part of the first chamber 26 such that the open top end 24 is broader than the bottom edge 52. In this way, the tapering section forms a handle. As it is preferred that the first chamber 26 be compressible, according to the depicted embodiments, the first chamber 26 is preferably compressible laterally, such that the individual dispensing the medication would squeeze along the tapering area.

Figure 23:
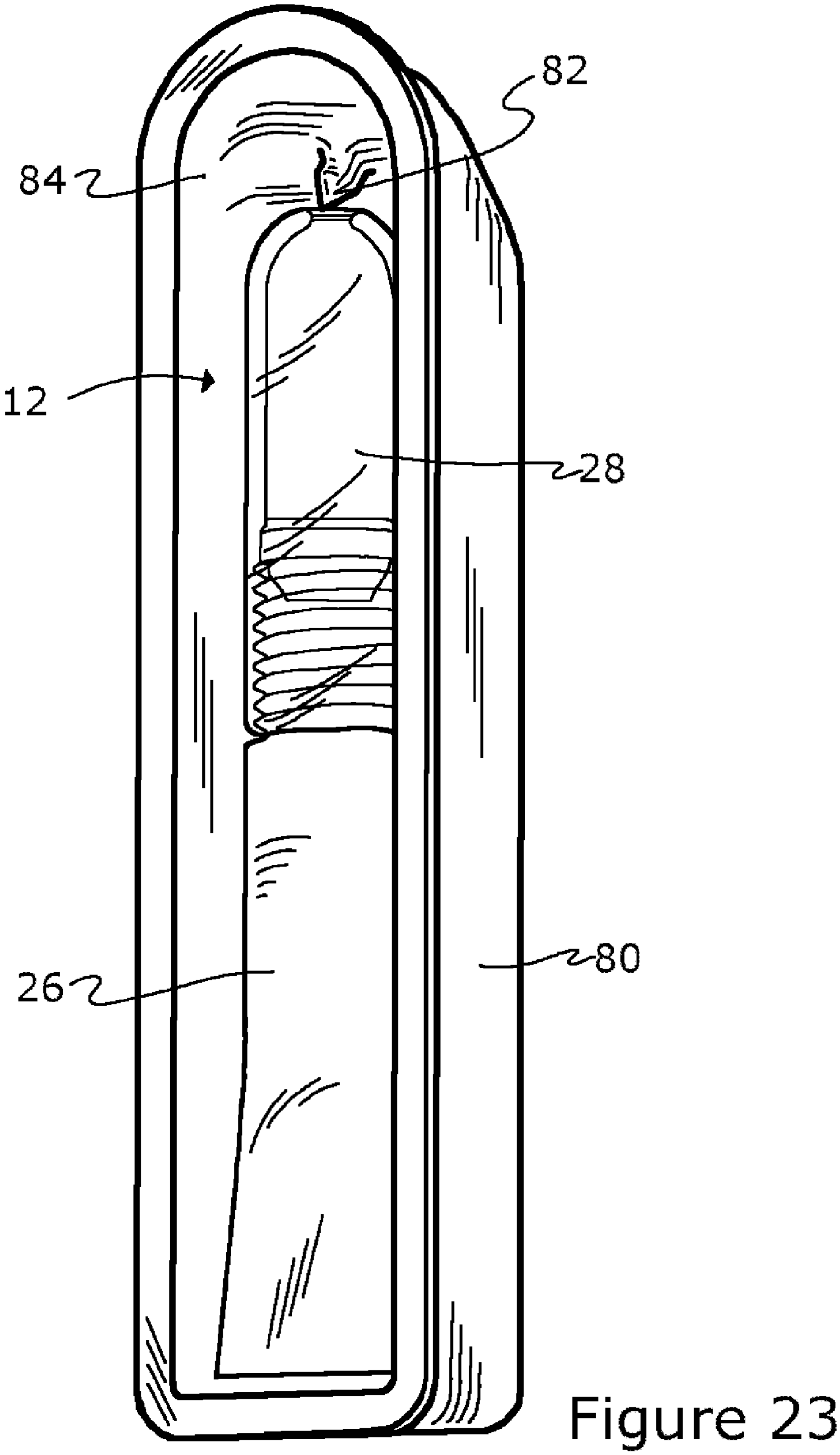
FIG. 23 is an isometric view of the front and right sides of a medication dispenser within a storage container according to the first embodiment of a dispensing system.
Figure 24:
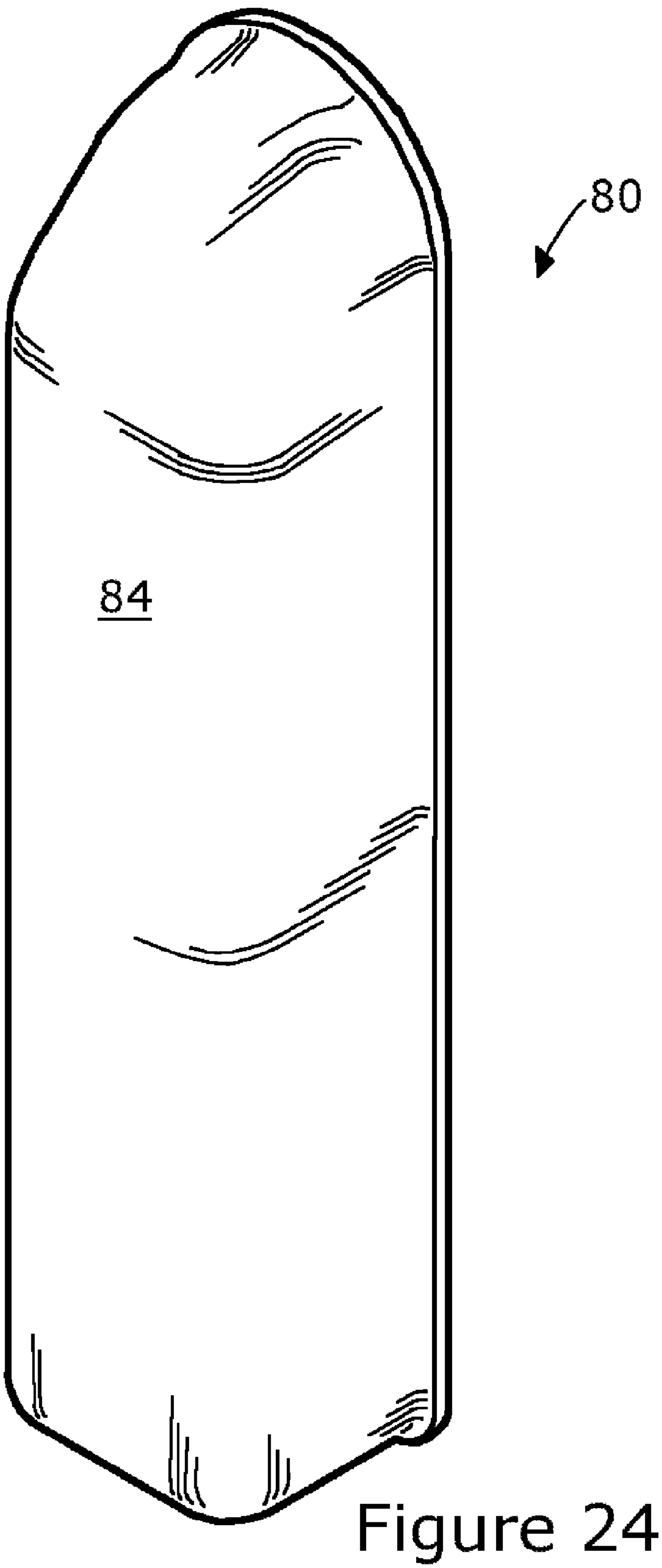
FIG. 24 is an isometric view of the back, top, and left sides of a medication dispenser within a storage container according to the first embodiment of a dispensing system.
Figure 25:
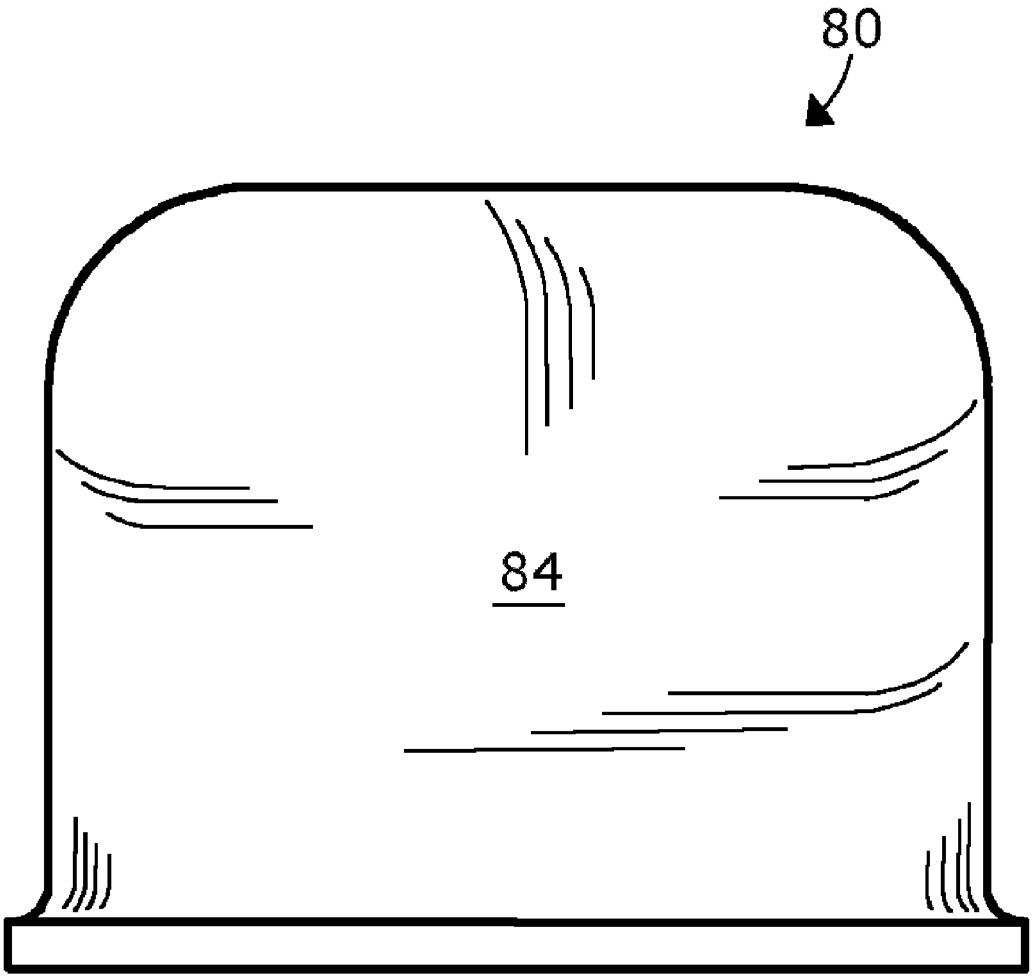
FIG. 25 is an elevation view of the bottom of a medication dispenser within a storage container according to the first embodiment of a dispensing system.
Figure 26:
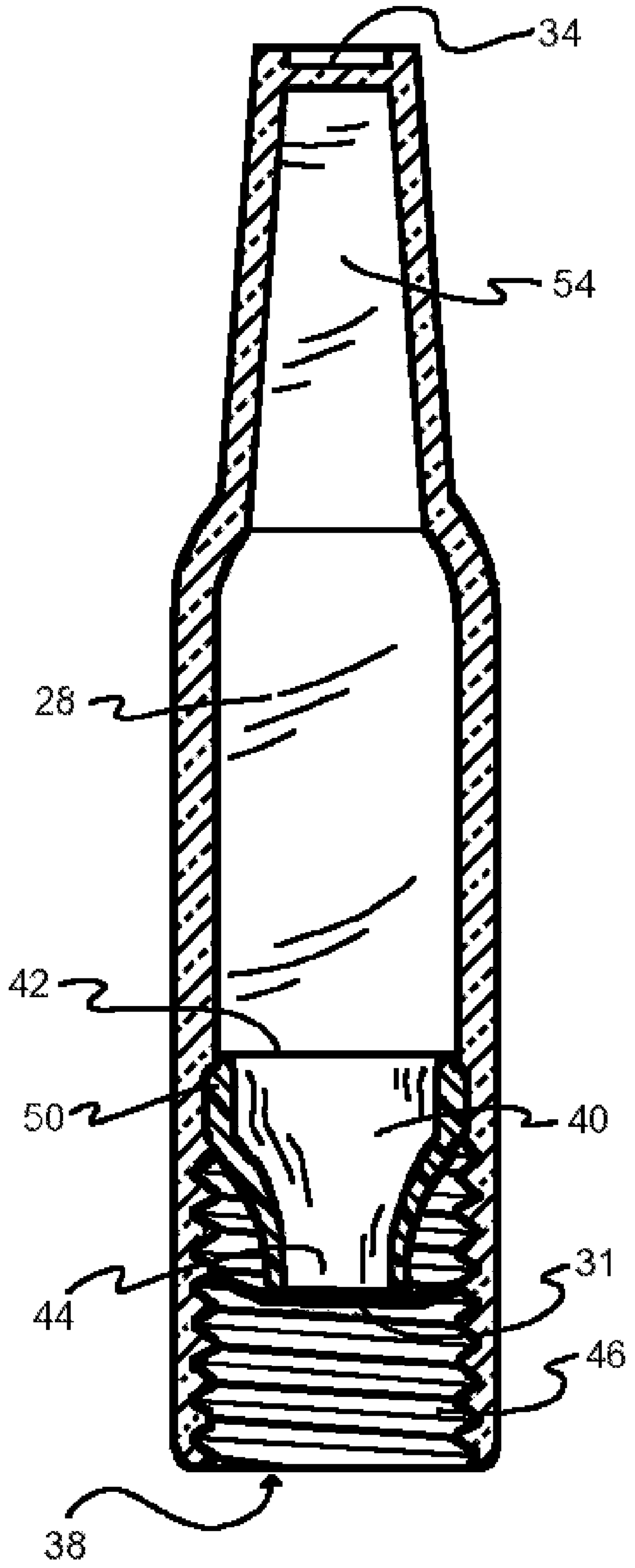
FIG. 26 is a cross-sectional, elevation view from the left side, of a second chamber and breaker ring of a medication dispenser according to a fourth embodiment of a dispensing system.

According to some embodiments, the openable tip 34 of the dispenser 12 is puncturable. As such, the dispenser 12 is configured to be utilized as the puncturable, compressible ampule of the oral liquid medication dispensing system for dispensing measured dosages of selected oral medication described in U.S. Pat. No. 7,452,350, the disclosure of which is incorporated herein by reference in its entirety. Further, the dispenser 12 is configured to be utilized with the storage container 80 of the depicted dispensing system, as shown in FIGS. 23 through 25. The depicted storage container 80 of the dispensing system includes a container wall 84 that is configured to receive within the dispenser 12. The storage container 80 includes a puncturing device 82 (FIG. 23). Preferably, the puncturing device 82 is formed within a bottom portion of the container wall 84 of the storage device 80. In other embodiments, the puncturing device 82 is fixedly attached to the container wall 84. The puncturing device 82 protrudes from the container wall 84, and the puncturing device 82 is configured to enable puncturing of a puncturable openable tip 34 of the first chamber 26 of the dispenser 12. More particularly, the puncturing device 82 is configured such that manipulation of the dispenser 12 so as to position the openable tip 34 to be in forced contact with the puncturing device 82 will result in puncturing of the openable tip 34 with the opening 16 being created thereby. Preferably, the puncturing device 82 is calibrated to create an opening 16 of a pre-determined size. Also, preferably, the puncturing device 82 is recessed within the storage container 80, as shown in FIG. 23, so as to avoid unintended interaction with external items and to lessen the risk of unintended interaction with a user's fingers. The container wall 84 further defines an upper ridge forming the upper border of the storage container 80. In some embodiments, the storage container 80 is covered with a removable covering along the upper ridge, thereby providing additional protection to the dispenser 12 within the storage container 80 during transport or otherwise before use thereof.

The exemplary embodiments shown in the figures and described above illustrate, but do not limit, the dispensing system. It should be understood that there is no intention to limit the dispensing system to the specific form disclosed; rather, the dispensing system is to cover all modifications, alternative constructions, and equivalents falling within the spirit and scope of the dispenser as defined in the claims. For example, while the dispensing system is not limited to use with orally-administered medication, it is expected that various embodiments of the dispensing system will be particularly useful in such applications. Further, while the chambers of the dispensing system preferably interconnect via screw threads, in other embodiments, the chambers interact via a close-fitting slideable or push interaction or a plunger interaction. Hence, the foregoing description should not be construed to limit the scope of the invention, which is defined in the following claims.

Accordingly, while there is shown and described the present preferred embodiments of the dispensing system, it is to be distinctly understood that this dispensing system is not limited thereto but may be variously embodied to practice within the scope of the following claims. From the foregoing description, it will be apparent that various changes may be made without departing from the spirit and scope of the invention, as defined by the following claims.

What is claimed is:

1. A medication dispenser comprising:

a first chamber, said first chamber having an open top end, said first chamber being at least partially compressible;

a reconstituting fluid contained within said first chamber;

a first breakable membrane covering said open top end of said first chamber;

a second chamber, said second chamber having an open bottom end and an openable tip, said second chamber being selectively joinable to said first chamber;

a pre-selected quantity of medication contained within said second chamber; and a breaker ring within said second chamber, said breaker ring having a lower edge directed away from said openable tip, said lower edge of said of said breaker ring being configured to be received within said open top end of said first chamber;

said second chamber being configured to selectively retract at least partially within said first chamber to transition said medication dispenser from an extended position, in which said lower edge of said breaker ring is not in contact with said first breakable membrane and not in contact with said reconstituting fluid, to a compact position, in which said lower edge of said breaker ring is received within said open top end of said first chamber;

said breaker ring being configured to break through said first breakable membrane when said second chamber is retracted to transition said medication dispenser from said extended position to said compact position;

said openable tip being configured to be selectively openable to form an opening;

whereby retracting of said second chamber at least partially within said first chamber to transition said medication dispenser from said extended position to said compact position causes said breaker ring to break open said first breakable membrane such that said medication within said second chamber and said reconstituting fluid within said first chamber mix to form a medication mixture; and whereby, following opening of said openable tip, compression of said first chamber while said medication dispenser is in said compact position forces said medication mixture out of said first chamber, through said breaker ring, and out of said second chamber via said opening.

2. The medication dispenser of claim 1, further comprising:

a second breakable membrane covering said lower edge of said breaker ring;

whereby retracting of said second chamber at least partially within said first chamber to transition said medication dispenser from said extended position to said compact position causes said breaker ring to break open said second breakable membrane and said first breakable membrane.

3. The medication dispenser of claim 1, wherein said second chamber further comprises a tapering portion proximate to said openable tip, said tapering portion being configured to accommodate attachment of a catheter to said medication dispenser.

4. The medication dispenser of claim 1, wherein said first chamber further includes an internal surface and first screw threads lining at least part of said internal surface;

said second chamber further includes an external surface and second screw threads lining at least part of said external surface;

said first chamber and said second chamber being selectively joinable via interaction of said first screw threads and said second screw threads; and said second chamber being configured to selectively retract at least partially within said first chamber via twisting said first chamber relative to said second chamber.

5. The medication dispenser of claim 1, wherein said medication contained within said second chamber is a powder.

6. The medication dispenser of claim 1, wherein said second chamber comprises a translucent plastic.

7. The medication dispenser of claim 1, wherein said openable tip is puncturable.

8. The medication dispenser of claim 1, wherein said second chamber comprises a noncompressible plastic.

9. The medication dispenser of claim 1, wherein said first chamber tapers in width from said open top end to a bottom edge.

* * * * *